United States Patent [19]

Gaeta et al.

[11] Patent Number: 5,559,103
[45] Date of Patent: Sep. 24, 1996

[54] BIVALENT SIALYL X SACCHARIDES

[75] Inventors: Federico C. A. Gaeta, Foster City; Shawn A. DeFrees, San Marcos, both of Calif.

[73] Assignee: Cytel Corporation, San Diego, Calif.

[21] Appl. No.: 278,020

[22] Filed: Jul. 20, 1994

Related U.S. Application Data

[63] Continuation-in-part of Ser. No. 95,657, Jul. 21, 1993, abandoned.

[51] Int. Cl.$^6$ .......................... A61K 31/725; C08B 37/00
[52] U.S. Cl. ................... 514/54; 514/62; 514/886; 514/887; 536/53; 536/54; 536/55; 536/55.1; 536/55.2; 530/395; 530/396
[58] Field of Search .................. 514/54, 62, 886, 514/887; 536/53, 54, 55, 55.1, 55.2; 530/395, 396

[56] References Cited

U.S. PATENT DOCUMENTS

| | | | |
|---|---|---|---|
| 4,235,871 | 11/1980 | Papahadjopoulos et al. | 424/450 |
| 4,501,728 | 2/1985 | Geho et al. | 424/450 |
| 4,837,028 | 6/1989 | Allen | 424/1.21 |
| 5,079,353 | 1/1992 | Ratcliffe et al. | 536/53 |
| 5,143,712 | 9/1992 | Brandley et al. | 424/1.73 |
| 5,180,674 | 1/1993 | Roth | 435/293.1 |
| 5,211,936 | 5/1993 | Brandley et al. | 424/1.73 |
| 5,211,937 | 5/1993 | Brandley et al. | 424/1.73 |
| 5,220,008 | 6/1993 | Sabesan | 536/4.1 |
| 5,254,676 | 10/1993 | Sabesan | 536/4.1 |
| 5,296,594 | 3/1994 | Ratcliffe et al. | 536/53 |
| 5,352,670 | 10/1994 | Venot et al. | 514/54 |

FOREIGN PATENT DOCUMENTS

| | | |
|---|---|---|
| WO91/19501 | 12/1991 | WIPO. |
| WO91/19502 | 12/1991 | WIPO. |
| WO92/16640 | 10/1992 | WIPO. |
| WO92/22301 | 12/1992 | WIPO. |
| WO92/22564 | 12/1992 | WIPO. |

OTHER PUBLICATIONS

Graber et al., *J. Immunol.*, 145:819 (1990).
Bevilacqua et al., *Science*, 243:1160–1165 (1989).
Hession et al., *Proc. Natl. Acad. Sci.*, 87:1673–1677 (1990).
Bevilacqua et al., *Proc. Natl. Acad. Sci.*, 84:9238–9242 (1987).
Siegellman et al., *Science*, 243:1165–1172 (1989).
Lasky et al., *Cell*, 56:1045–1055 (1989).
Drickamer, *J. Biol. Chem.*, 263:9557–9560 (1988).
Springer et al. *Nature*, 349:196 (1991).
Lasky, *Science*, 258:964 (1992).
Phillips et al., *Science*, 250:1130 (1990).
Walz et al., *Science*, 250:1132 (1990).
Berg et al., *J. Biol Chem.*, 23:14869 (1991).
Mulligan et al., *Nature*, 364:149 (1993).
Sabesan et al., *J. Am. Chem. Soc.*, 114:8363 (1992).
Ichikawa et al., *J. Am. Chem. Soc.*, 114:9283 (1992).
Palic et al., *Carbohydr. Res.*, 190:1 (1989).
Lobb et al., *J. Immunol.*, 147:124–129 (1991).
Langer, *Science*, 249:1527–1533 (1990).
Green et al., *Biochem. Biophys. Res. Commun.* Oct. 15, 1992, 188(1), 244–251.
Needham et al., *Proc. Nat. Acad. Sci. USA* Feb. 1993, 90, 1359–1363.

(List continued on next page.)

*Primary Examiner*—Gary L. Kunz
*Assistant Examiner*—Kathleen Kahler Fonda
*Attorney, Agent, or Firm*—Townsend and Townsend and Crew LLP

[57] ABSTRACT

The present invention relates to bivalent sialyl Lewis X saccharide compounds that inhibit cellular binding to a selectin receptor. Pharmaceutical compositions containing a compound of Formula I, and processes for making and using the same are disclosed. A contemplated bivalent sialyl Lewis X saccharide compound has a structure that corresponds to Formula I, below,

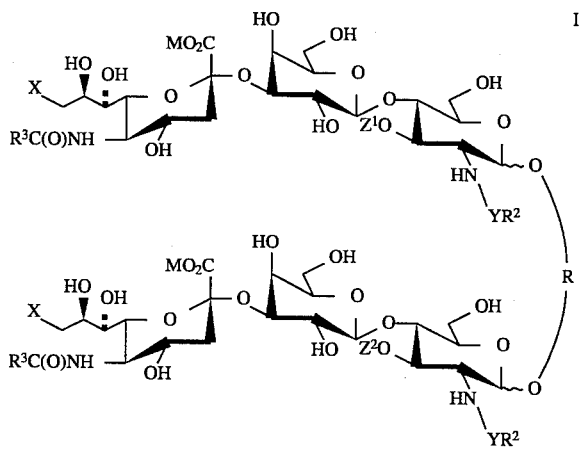

wherein R is a directly linked divalent monosaccharide unit;

Y is selected from the group consisting of C(O), SO$_2$, HNC(O), OC(O) and SC(O);

R$^2$ is selected from the group consisting of a C$_1$–C$_6$ hydrocarbyl, an aryl, a substituted aryl and a phenyl C$_1$–C$_3$ alkylene group, wherein an aryl group has one six-membered aromatic ring or two fused six-membered aromatic rings, which ring or rings are hydrocarbyl, monoazahydrocarbyl, or diazahydrocarbyl rings, and a substituted aryl group is a before-mentioned aryl group having a substituent selected from the group consisting of halo, trifluoromethyl, nitro, C$_1$–C$_6$ alkyl, C$_1$–C$_6$ alkoxy, amino, mono-C$_1$–C$_6$ alkylamino, di-C$_1$–C$_6$ alkylamino, benzylamino and C$_1$–C$_6$ alkylbenzylamino;

R$^3$ is methyl or hydroxymethyl;

X is selected from the group consisting of hydroxyl, C$_1$–C$_6$ acyloxy, C$_2$–C$_6$ hydroxylacyloxy, halo and azido;

Z$^1$ and Z$^2$ are α-L-fucosyl or hydrogen (H), but at least one of Z$^1$ and Z$^2$ is α-L-fucosyl; and M is a proton (H$^+$) or a pharmaceutically acceptable cation.

27 Claims, 1 Drawing Sheet

OTHER PUBLICATIONS

DeFrees et al. *J. Am. Chem. Soc.* Aug. 11, 1993, 115(16), 7549–7550.

Nimtz et al. *Eur. J. Biochem.* 1993, 213(1), 39–56.

Hotta et al. *J. Carbohydr. Chem.* Mar. 7, 1994, 13(2), 175–191.

BIVALENT SIALYL X SACCHARIDES

CROSS-REFERENCE TO RELATED APPLICATION

This is a continuation-in-part of application Ser. No. 08/095,657, filed Jul. 21, 1993, whose disclosures are incorporated by reference.

TECHNICAL FIELD

The present invention relates to compounds that inhibit adhesion between cells, and more particularly relates to saccharide compounds that contain two sialyl Lewis X (SLe$^x$) moieties that inhibit such cellular adhesion, compositions containing the same and methods for preparing and using those compounds.

BACKGROUND ART

Vascular endothelial cells and blood platelets play key roles in a number of biological responses by selectively binding certain cells, for instance phagocytic leukocytes, in the bloodstream. For example, endothelial cells preferentially bind monocytes and granulocytes prior to their migration through the blood vessel wall and into surrounding tissue in an inflammatory response.

Certain inflammation-triggering compounds are known to act directly on the vascular endothelium to promote the adhesion of leukocytes to vessel walls. Cells then move through the walls and into areas of injury or infection.

Intercellular adhesion to vascular endothelium is also thought to be involved in tumor metastasis. Circulating cancer cells apparently take advantage of the body's normal inflammatory mechanisms and bind to areas of blood vessel walls where the endothelium is activated.

Blood platelets are also involved in similar responses. Platelets are known to become activated during the initiation of hemostasis and undergo major morphological, biochemical, and functional changes (e.g., rapid granule exocytosis, or degranulation), in which the platelet alpha granule membrane fuses with the external plasma membrane. As a result, new cell surface proteins become expressed that confer on the activated platelet new functions, such as the ability to bind both other activated platelets and other cells. Activated platelets are recruited into growing thrombi, or are cleared rapidly from the blood circulation. Activated platelets are known to bind to phagocytic leukocytes, including monocytes and neutrophils. Examples of pathological and other biological processes that are thought to be mediated by this process include atherosclerosis, blood clotting and inflammation.

Recent work has revealed that specialized cell surface receptors on endothelial cells and platelets, designated endothelial leukocyte adhesion molecule-1 (ELAM-1) and granule membrane protein-140 (GMP-140), respectively, are involved in the recognition of various circulating cells by the endothelium and platelets. For example, ELAM-1 has been shown to mediate endothelial leukocyte adhesion, which is the first step in many inflammatory responses. Specifically, ELAM-1 binds human neutrophils, monocytes, eosinophils, certain T-lymphocytes [Graber et al., *J. Immunol.*, 145:819 (1990)], NK cells, and the promyelocytic cell line HL-60.

ELAM-1 is inducibly expressed on vascular endothelial cells [Bevilacqua et al., *Science*, 243:1160–1165 (1989) and Hession et al., *Proc. Natl. Acad. Sci.*, 87:1673–1677 (1990)]. This receptor has been demonstrated to be induced by inflammatory cytokines such as interleukin Iβ (IL-Iβ) and tumor necrosis factor α (TNFα), as well as bacterial endotoxin (lipopolysaccharide) [Bevilacqua et al., *Proc. Natl. Acad. Sci.*, 84:9238–9242 (1987)]. These compounds augment polymorphonuclear leukocyte (neutrophil), and monocyte adhesion [Bevilacqua et al., *Proc. Natl. Acad. Sci.*, 84:9238–9242 (1987)].

GMP-140 (also known as PADGEM) is present on the surface of platelets and endothelial cells, where it mediates platelet-leukocyte and endothelium-leukocyte interactions, [Geng et al., *Nature*, 343:757–760 (1990)]. Thus, for example, activated platelets that express GMP-140 on their surfaces are known to bind to monocytes and neutrophils [Jungi et al., *Blood*,m 67:629–636 (1986)], and also to bind monocyte-like cell lines, e.g., HL60 and U937 [Jungi et al., *Blood*, 67:629–636 (1986); Silverstein et al., *J. Clin. Invest.*, 79:867–874 (1987)].

GMP-140 is an alpha granule membrane protein of molecular mass 140,000 that is expressed on the surface of activated platelets upon platelet stimulation and granule secretion [Hsu-Lin et al., *J. Clin. Chem.*, 259:9121–9126 (1984); Stenberg et al., *J. Cell Biol.*, 101:880–886 (1985); Berman et al., *J. Clin. Invest.*, 78:130–137 (1986)]. It is also found in megakaryocytes [Beckstead et al., *Blood*, 67:285–293 (1986)], and in endothelial cells [McEver et al., *Blood*, 70:335a (1987)]within the Weibel-Palade bodies [Bonfanti et al., *Blood*, 73:1109–1112 (1989)]. Furie et al., U.S. Pat. No. 4,783,330, describe monoclonal antibodies reactive with GPM-140.

A third receptor is the lymphocyte homing receptor, MEL-14 antigen or LAM-1 [Gallatin et al., *Nature*, 304:30–34 (1983); Siegellman et al., *Science*, 243:1165–1172 (1989); Rosen, *Cell Biology*, 1:913–919 (1989); and Lasky et al., *Cell*, 56:1045–1055 (1989)]. In addition to lymphocyte homing, MEL-14 antigen/LAM-1 is believed to function early in neutrophil binding to the endothelium.

The term "selectin" has been suggested for a general class of receptors, which includes ELAM-1 and GMP-140 and MEL-14, because of their lectin-like domain and the selective nature of their adhesive functions. The structure and function of selectin receptors has been elucidated by cloning and expression of full length cDNA encoding each of the above receptors [Bevilacqua et al., *Science*, 243:1160–1165 (1989), (ELAM-1); Geng et al., *Nature*, 343:757–760 (1990), (GMP-140); and Lasky et al., *Cell*, 56:1045–1055 (1989), (MEL-14 antigen)].

The extracellular portion of selectins can be divided into three segments based on homologies to previously described proteins. The N-terminal region (about 120 amino acids) is related to the C-type mammalian lectin protein family as described by Drickamer, *J. Biol. Chem.*, 263:9557–9560 (1988) that includes low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

The above-described selectins are now referred to as E-, P- and L-selectins that correspond to ELAM-1, GMP-140 and MEL-14 antigen/LAM-1, respectively. Cell adhesion of leukocytes to endothelial cells involves the interaction of E-, P- and L-selectins with their respective receptors. [Paulson, J. C. in "Adhesion, Its role in Inflammatory Disease", (Harlan, J.; Liu, D. eds.) W. H. Freeman, New York, Chapt. 2, p.19 (1992); Springer et al. Nature, 349:196 (1991); Lasky, *Science*, 258:964 (1992); Kobata et al. in "Cell Surface Carbohydrates and Cell Development", (Fukuda, M., Ed.), CRC Press, London, p.1 (1992)]. Although the natural ligands have not been completely characterized, the partial chemical structure of the ligands for E- and P-selectin has been shown to contain the tetrasaccharide sialyl Lewis X (SLe$^x$) [Phillips et al., *Science*, 250:1130 (1990); Walz et al., *Science*, 250:1132 (1990); Lowe et al., *Cell*, 63:475 (1990); Polley et al., *Proc. Natl. Acad. Sci. USA*, 88:6224 (1991); Zhou et al., *J. Cell Biol.*, 88:557 (1991); U.S. Pat. Nos. 5,079,353 and 5,296,594], although sialyl Lewis A type structures may also act as receptor ligands. [Berg et al., *Biochem Biophys. Res. Commun.*, 184:1048 (1992); Berg et al., *J. Biol Chem.*, 23:14869 (1991); Handa et al., *Biochem. Biophys. Res. Commun.*, 181:1223 (1991)]. Sialyl Le$^x$ glycal has also been shown to inhibit binding to E-selectin. [DeFrees et al., *J. Am. Chem. Soc.*, 115:7549 (1993).]

The ligand for L-selectin has also been proposed to contain an SLe$^x$ type structure in which the sialic acid is replaced with a sulfate group. [Yuen et al., *Biochemistry*, 31:9126 (1992)]. Application WO 92/22564 discloses sulfate, phosphate and carboxylate derivatives of Lewis X and Lewis a compounds that lack a sialyl group, but are said to provide enhanced immunosuppressing or tolerogenic properties over derivatives lacking the sulfate, phosphate or carboxylate substituents.

Published International application WO 91/19501 and WO 91/19502 disclose that oligosaccharides containing the pentameric and hexameric structures shown below inhibited selective intercellular binding between cells containing the ligand (below) and those containing a selectin receptor and that the penta- and hexasaccharides provided better inhibition than did SLe$^x$:

NeuAcα2→3βGalβ1→4(Fucα1→3)GlcNAcβ1,3Galβ-;

NeuAcα2→3βGalβ1→4(Fucα1→3)GlcNAcβ1,3Galβ1, 4Glc-; and

NeuAcα2→3βGalβ1→4(Fucα1→3)GlcNAc=SLe$^x$.

Mulligan et al., *Nature*, 364:148 (1993) showed that infusion of SLe$^x$ or a SLe$^x$-galactoside that are ligands for P-selectin reduced lung injury and reduced accumulation of neutrophils in cobra venum-infused rats. U.S. Pat. No. 5,143,712 and application WO 92/22301 similarly and separately disclose that LacNAc linear multimers having a non-reducing terminal SLe$^x$ or sialyl-LacNAc group can be useful in suppressing an immune response.

Free oligosaccharides, both natural and synthetic, generally exhibit weak binding to lectin receptors, a deficiency that is often overcome by multivalent interactions. [Kingery-Wood et al., *Am. Chem. Soc.*, 114:7303 (1992); Weis et al., *Nature*, 360:127 (1992); Sabesan et al., *J. Am. Chem. Soc.*, 114:8363 (1992)]. The fact that monomeric SLe$^x$ binds weakly to E- and P-selectin, [Nelson et al., *J. Clin. Invest.*, 91:1157 (1993)], coupled with recent observations [Moore et al., *J. Cell Biol.*, 118:445 (1992] that suggest a clustering of SLe$^x$ type structures on the putative glycoprotein ligands reinforces the concept that SLe$^x$-selectin interactions are multimeric in vivo. Sialyl Lewis X structures on the natural selectin ligand could exist as either N- or O-linked oligosaccharides, [Kobata et al., in "Cell Surface Carbohydrates and Cell Development", (Fukuda, M., Ed.), CRC Press: London, p.1 (1992)] and multiple copies of SLe$^x$ may be presented as clusters of single SLe$^x$ units in close proximity or as multiple SLe$^x$ structures on polyantennary oligosaccharide chains.

The present invention, discussed hereinafter, illustrates the capacity of a branched oligosaccharide containing two copies of the SLe$^x$ glycotope to inhibit binding between cells containing an E-selectin receptor and cells that express an E-selectin ligand, such as activated endothelial cells and neutrophils and contemplates several bivalent SLe$^x$ inhibitor analogs that can mimic structures found in N- and O-glycans.

BRIEF SUMMARY OF THE INVENTION

The present invention contemplates a bivalent sialyl Lewis X (SLe$^x$) saccharide, as well as a composition containing the same and a process for using such a compound to inhibit adhesion between cells that express a selectin receptor such as the E-selectin receptor on their surfaces and cells that express SLe$^x$ on their surfaces. A contemplated compound has a structure that can be depicted by the structural formula

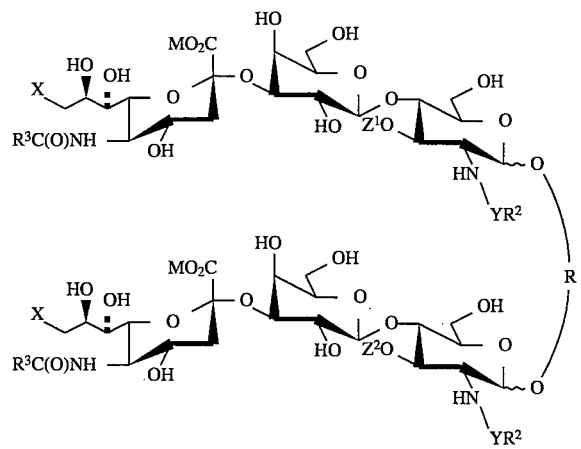

wherein R is a directly linked divalent monosaccharide unit;

Y is selected from the group consisting of C(O), SO$_2$, HNC(O), OC(O) and SC(O);

R$^2$ is selected from the group consisting of a C$_1$–C$_{18}$ aliphatic, an aryl, a substituted aryl and a phenyl C$_1$–C$_3$ alkylene, wherein an aryl group has one six-membered aromatic ring or two fused six-membered aromatic rings, which ring or rings are hydrocarbyl, monoazahydrocarbyl, or diazahydrocarbyl rings, and a substituted aryl group is a before-mentioned aryl group having a substituent selected from the group consisting of halo, trifluoromethyl, nitro, C$_1$–C$_6$ alkyl, C$_1$–C$_6$ alkoxy, amino, mono-C$_1$–C$_6$ alkylamino, di-C$_1$–C$_6$ alkylamino, benzylamino and C$_1$–C$_6$ alkylbenzylamino;

R$^3$ is methyl or hydroxymethyl;

X is selected from the group consisting of hydroxyl, C$_1$–C$_6$ acyloxy, C$_1$–C$_6$ hydroxylacyloxy, halo and azido;

Z$^1$ and Z$^2$ are α-L-fucosyl or hydrogen (H), but at least one of Z$^1$ and Z$^2$ is α-L-fucosyl; and M is a proton (H$^+$) or a pharmaceutically acceptable cation.

In preferred embodiments, R is depicted by a structure selected from the group consisting of

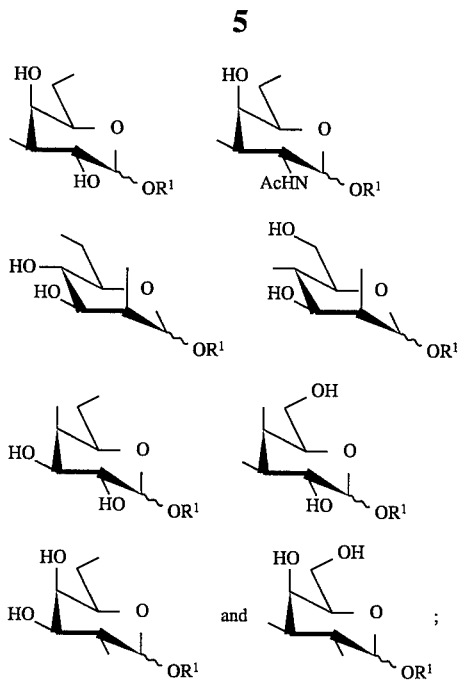

wherein $R^1$ is selected from the group consisting of hydrogen, a $C_1$–$C_{18}$ straight chain, branched chain or cyclic hydrocarbyl, a $C_1$–$C_6$ alkyl $C_1$–$C_5$ alkylene ω-carboxylate, and a ω-tri($C_1$–$C_4$ alkyl/phenyl)silyl $C_2$–$C_4$ alkylene group, or $CR^1$ together form a $C_1$–$C_{18}$ straight chain, branched chain or cyclic hydrocarbyl carbamate.

In particularly preferred practice, both $Z^1$ and $Z^2$ are α-L-fucosyl. Also in preferred embodiments, Y is a carbonyl group so that $YR^2$ forms an amide bond with the amine group of the saccharide rings. Multimeric forms of a contemplated bivalent $SLe^x$ compound are also contemplated.

A composition containing an amount of a before-describe bivalent $SLe^x$ saccharide sufficient to inhibit the binding of cells that express $SLe^x$ on their surfaces to a selectin is also contemplated. The bivalent $SLe^x$ saccharide is dissolved or dispersed in a pharmaceutically acceptable diluent in such a composition.

A process for inhibiting the adhesion between selectin and cells that express $SLe^x$ on their cell surfaces is also contemplated. In accordance with that process, cells that express $SLe^x$ on their cell surfaces, selectin and an adhesion-inhibiting amount of a before-described bivalent $SLe^x$ saccharide are admixed in an aqueous medium.

The $IC_{50}$ value for the inhibition of binding or adhesion between selectin and $SLe^x$-bearing cells for a contemplated bivalent $SLe^x$ saccharide is conveniently compared to that of $SLe^x$ itself. That comparison is conveniently expressed as a ratio of the $IC_{50}$ value of $SLe^x$ to the $IC_{50}$ value of a contemplated compound in an in vitro assay using a recombinant E-selectin that contains the amino-terminal 527 amino acid residues of that protein bound to a solid phase support. The ratio is greater than two for a contemplated compound; i.e., the $IC_{50}$ value for a contemplated compound is less than one-half that for $SLe^x$.

BRIEF DESCRIPTION OF THE DRAWING

In the drawing forming a portion of this disclosure.

DETAILED DESCRIPTION OF THE INVENTION

A. The Compounds

Figure 1:
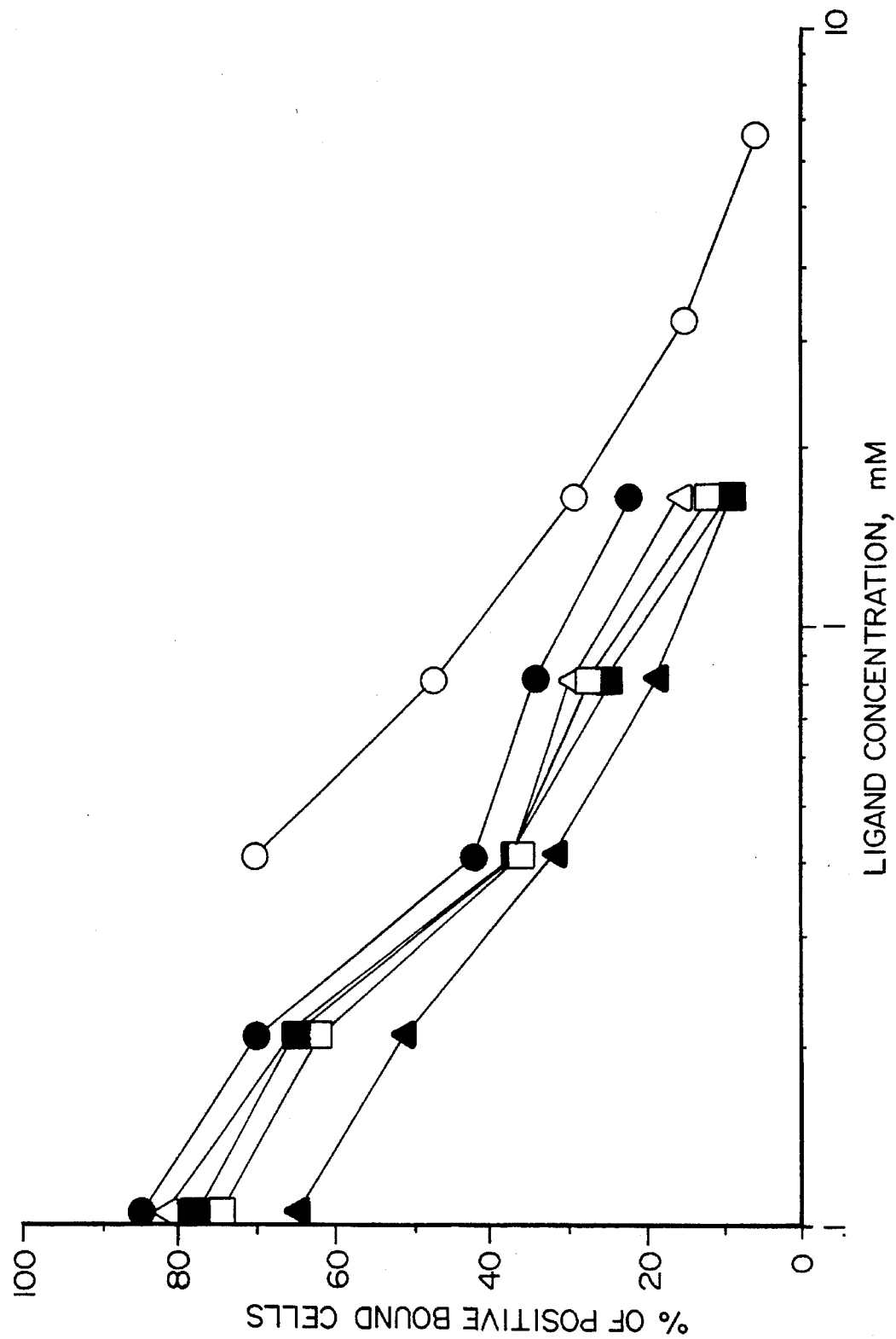
FIG. 1 is a graph that illustrates the inhibition of HL-60 cell adhesion to recombinant soluble E-selectin-coated plates. The ordinate is in units of the percentage of positive bound cells. The abscissa is in units of millimolar (mM) inhibitor concentration. The compounds assayed were: Compound 1 (closed triangles), Compound 23 (open squares), Compound 22 (closed squares), Compound 21 (open triangles), Compound 20 (closed circles) and Compound Z (open squares).

A compound contemplated by the present invention is a saccharide that contains two glycosidically linked sialyl Lewis X ($SLe^x$) moieties or analogues thereof that is usually referred to as a bivalent $SLe^x$ compound. A contemplated compound inhibits the binding between E-selectin (also referred to as the endothelial leukocyte adhesion molecules or ELAM-1) that is expressed on the surface of endothelial cells during inflammation, and a glycotope ligand structure displayed on the surface of neutrophils, HL-60 and other cells.

A contemplated compound has the structure of Formula I, below

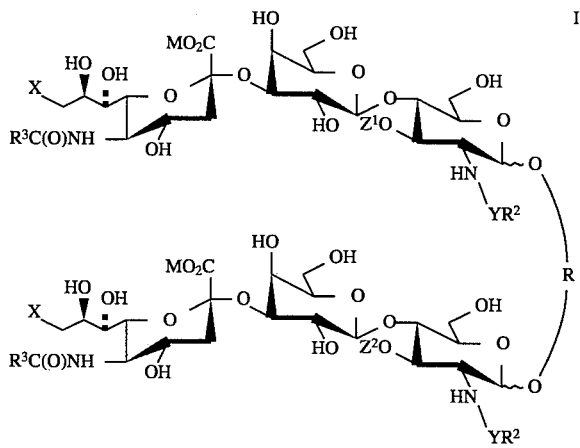

wherein R is a directly linked bivalent monosaccharide unit;

Y is selected from the group consisting of C(O), $SO_2$, HNC(O), OC(O) and SC(O);

$R^2$ is selected from the group consisting of a $C_1$–$C_{18}$ aliphatic, an aryl, a substituted aryl and a phenyl $C_1$–$C_3$ alkylene group, wherein an aryl group has one six-membered aromatic ring or two fused six-membered aromatic rings, which ring or rings are hydrocarbyl, monoazahydrocarbyl, or diazahydrocarbyl rings, and a substituted aryl group is a before-mentioned aryl group having a substituent selected from the group consisting of halo, trifluoromethyl, nitro, $C_1$–$C_6$ alkyl, $C_1$–$C_6$ alkoxy, amino, mono-$C_1$–$C_6$ alkylamino, di-$C_1$–$C_6$ alkylamino, benzylamino and $C_1$–$C_6$ alkylbenzylamino;

$R^3$ is methyl or hydroxymethyl;

X is selected from the group consisting of hydroxyl, $C_1$–$C_6$ acyloxy, $C_2$–$C_6$ hydroxylacyloxy, halo and azido;

$Z^1$ and $Z^2$ are α-L-fucosyl or hydrogen (H), but at least one of $Z^1$ and $Z^2$ is α-L-fucosyl; and M is a proton ($H^+$) or a pharmaceutically acceptable cation.

The divalent monosaccharide R group is directly linked to the depicted two oligosaccharide groups. That is, two oxygen atoms of ring or side chain saccharide hydroxyl groups of the monosaccharide form a glycosidic bond with each depicted tri- or tetrasaccharide, without the intervention of spacer or other linking group.

The glycosidic bonds formed are shown as wavy lines to indicate that both α- and β-bonding to the tri- or tetrasaccharides are contemplated. Wavy lines are used in exemplary structures A–H below and elsewhere herein with the same meaning.

The divalent monosaccharide can be any $C_5$–$C_6$ cyclic sugar, but is preferably a hexose, and preferably has a pyranose structure. Exemplary divalent monosaccharides include ribose, arabinose, lyxose, xylose, glucose, galactose, mannose, fucose, fructose, allose, altrose, gulose, idose and talose. The 2-deoxy forms of the above sugars are also contemplated such 2--deoxyribose, and 2-deoxyglucose, as are the 2-deoxy-2-$C_1$–$C_6$ acylamino such as N-acetylglucosamine and N-acetylgalactosamine.

An exemplary preferred monosaccharide unit has a structure that is illustrated in structures A–H, below, with a divalent galactosyl unit being particularly preferred.

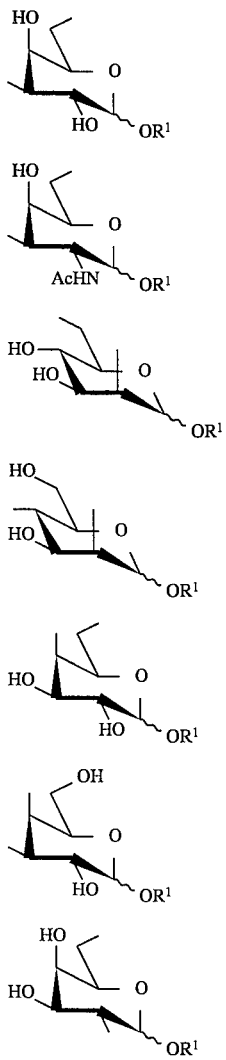

and

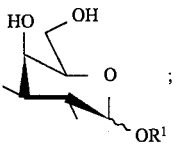

wherein $R^1$ is selected from the group consisting of hydrogen, a $C_1$–$C_{18}$ straight chain, branched chain or cyclic hydrocarbyl, a $C_1$–$C_6$ alkyl $C_1$–$C_5$ alkylene ω-carboxylate, and an ω-tri($C_1$–$C_4$ alkyl/phenyl)silyl $C_2$–$C_4$ alkylene group, or $OR^1$ together form a $C_1$–$C_{18}$ straight chain, branched chain or cyclic hydrocarbyl carbamate.

An $R^1$ group thus forms a glycoside and preferably a β-glycoside with the saccharide ring system. That glycoside bond can be formed from a simple straight chain, branched chain or cyclic $C_1$–$C_{18}$ hydrocarbyl alcohol, from an ω-hydroxycarboxylic acid ester, from an ω-hydroxylated silylated alkyl group, or from a mono- or a disaccharide, or $OR^1$ together form a $C_1$–$C_{18}$ straight chain, branched chain or cyclic hydrocarbyl carbamate. Of the $C_1$–$C_{18}$ hydrocarbyl groups, a $C_1$–$C_6$ hydrocarbyl group such as a methyl or ethyl group, and a $C_1$–$C_6$ alkylene aryl group such as benzyl or phenethyl are preferred. Also preferred is a $C_1$–$C_6$ alkyl $C_1$–$C_5$ alkylene ω-carboxylate. $R^1$ can also be hydrogen.

Exemplary $R^1$ groups formed from simple precursor alcohol groups include $C_1$–$C_{18}$ straight chain, branched chain or cyclic hydrocarbyl groups. Illustrative of such groups are the $C_1$–$C_6$ alkyl groups such as methyl, ethyl, iso-propyl, butyl, sec-butyl, pentyl and hexyl, which are preferred, as well as their unsaturated counterparts, such as allyl, 3-butenyl, 2-but-3-enyl, and but-3-ynyl, as well as longer and cyclic hydrocarbyl groups such as benzyl, 4-methylcyclohexyl, decahydronaphthyl, nonyl, decyl (capryl), dodecyl (lauryl), dodec-7-enyl, myristyl, palmityl, stearyl, oleyl, linoleyl, linolenyl and ricinoleyl. Of the cyclic hydrocarbyl groups, a sub-set of $C_1$–$C_6$ alkylenearyl groups, where aryl is phenyl or 1-or 2-naphthyl, is preferred. Exemplary of such compounds are benzyl, phenethyl, and 1- and 2-naphthobenzyl [$(C_{10}H_7)CH_2$-]

A $C_1$–$C_{18}$ hydrocarbyl carbamate is prepared by reaction of an isocyanate corresponding to a before discussed $C_1$–$C_{18}$ hydrocarbyl group with the hydroxyl group of the reducing end sugar. For example, the 1-hydroxyl group of a terminal glucosyl unit can be reacted with ethylisocyanate to form the corresponding ethyl carbamate (urethane). The carbonyl group of the carbamate is not included in the number of hydrocarbyl carbon atoms.

A $C_1$–$C_6$ alkyl $C_1$–$C_5$-alkylene ω-carboxylate $R^1$ group is a $C_1$–$C_6$ alkyl ester of a $C_2$–$C_6$ ω-carboxylic acid. Such esters are prepared from precursor ω-hydroxycarboxylic acid $C_1$–$C_6$ esters whose hydroxyl groups are used to form the glycosidic bond. Exemplary ω-hydroxycarboxylate esters include methyl 2-hydroxyacetate, ethyl 3-hydroxypropionate, t-butyl 4-hydroxybutyrate, hexyl 5-hydroxypentanoate and methyl 6-hydroxyhexanoate. Thus, the hydroxyl and carboxyl groups are at the termini of the chain and are separated by 1–5 methylene groups. Methyl 6-hydroxyhexanoate acid is preferred.

A $C_1$–$C_6$ alkyl $C_1C_5$ alkylene ω-carboxylate is a particularly useful $R^1$ group in that it can be used as a means for linking a contemplated bivalent $SLe^x$ saccharide to another moiety as in the formation of liposomes, as well as for forming multimeric bivalent $SLe^x$ saccharide compounds. Thus, for example, a single tetramer can be formed by reaction of two moles of a bivalent $SLe^x$ saccharide such as Compound 1 with one mole of a $C_2$–$C_6$ straight chain di-primary amine such as ethylenediamine, 1,4-butanediamine or 1,6-hexanediamine to displace the $C_1$–$C_6$ ester groups and replace them with amides that link two bivalent $SLe^x$ saccharides together.

It is thus seen that multimeric forms of a contemplated bivalent $SLe^x$ saccharide are also contemplated and are readily prepared. In another illustration, reaction of a contemplated bivalent $SLe^x$ saccharide $C_1$–$C_6$ alkyl $C_1$–$C_5$ alkylene ω-carboxylate with an excess of an above di-primary amine provides a primary amine-terminated bivalent $SLe^x$ saccharide that can be reacted with a number of materials to provide multimeric forms of the bivalent molecule.

For example, complete reaction of such a primary amine-terminated molecule with trichlorotriazine provides a molecule containing six $SLe^x$ units (three groups of bivalent molecules). A similar hexa-$SLe^x$ result obtains by reaction with 1,3,5-benzenetricarboxylic acid chloride. Reaction of such a primary amine-terminated bivalent $SLe^x$ saccharide with a polyacrylic acid chloride can provide an average of about 1 to about 30 up to several hundred bivalent $SLe^x$ saccharide groups per polymer chain depending upon the polymer length (average molecular weights of 2000–4,000,000 are available from Aldrich Chemical Co.) and degree reaction obtained using well known reaction conditions for such reactions. Similar results can be obtained by reaction with a maleic anhydride-containing polymer or co-polymer, using the amine to open the anhydride to form an amide and carboxyl group.

A $C_1$–$C_6$ alkyl $C_1$–$C_5$ alkylene ω-carboxylate can also be used to link a plurality of bivalent $SLe^x$ saccharides to a polyamine such as polyethyleneimine (PEI), a long chain alkyl-substituted PEI [Johnson and Klotz, *Macromolecules*, 7:149 (1974)] or long chain alkyl-substituted quaternary ammonium PEI [Mirejovsky, *J. Org. Chem.*, 44.:4881–4886 (1979)]. Here, an amide-ester interchange reaction is typically used for bonding the amine groups to the bivalent $SLe^x$ saccharides.

An ω-tri($C_1$–$C_4$ alkyl/phenyl)silyl $C_2$–$C_4$ alkylene $R^1$ group is formed from a corresponding precursor alcohol whose tri-substituted silyl group is at the terminus (e-position) of the chain opposite the hydroxyl group. As is well known in the art, substituted silyl groups can include many combinations of $C_1$–$C_4$ alkyl and phenyl groups such as tri-$C_1$–$C_6$ alkyl, di-$C_1$–$C_4$ alkylphenyl, $C_1$–$C_4$ alkyldiphenyl and triphenyl. As such, "($C_1$–$C_4$ alkyl/phenyl)" is used to indicate that any combination of alkyl and phenyl groups can be present. Exemplary substituted silyl groups include trimethylsilyl, triphenylsilyl, di-t-butylmethylsilyl, dimethylphenylsilyl, t-butyldiphenylsilyl and the like.

The β-glycosyl bond formed with an $R^1$ group other than a carbamate can be prepared by well known organic chemical reactions with both the saccharides and other $R^1$ group precursors, as by reaction of a 1-halo saccharide with a hydroxyl of a desired $R^1$ group precursor alcohol in the presence of silver carbonate ($Ag_2CO_3$) or silver triflate, as well as by enzymatic means as with a glycosyl transferase for the saccharides.

Turning more specifically to the exemplary, bivalent directly linked monosaccharide R groups labeled A–H, it is seen that the R of A and B have the 3,6-bonding of β-galactosides and N-acetyl α-galactosides that are present in branched O-glycans, whereas the R of C and D have the 2,6- and 2,4-bonding of α-mannosides that are present in branched N-glycans. Remaining structures E–H illustrate different bonding structures based on galactose; a galactoside being preferred. The oxygen atoms present in the R A–H groups that form the glycosidic bonds with the $SLe^x$-type moieties shown in Formula I are shown in the upper and lower portions of structural Formula I, with open valences shown in the exemplary R structures.

Also not shown in any of the structural formulas herein are hydrogens bonded to carbon atoms that are not needed to show stereochemistry.

As noted before, Y can be one of a number of groups. When Y is C(O), $R^2Y$ is an acyl substituent group so that an amide is formed with the saccharide amine nitrogen atom. When Y is $SO_2$, $R^2Y$ is a sulfonyl substituent group so that a sulfonamide is formed with the saccharide amine nitrogen atom. When Y is HNC(O), $R^2Y$ is an aminocarbonyl substituent group so that a urea substituent is formed with that saccharide nitrogen atom. A urethane substituent is formed with the saccharide amine nitrogen where Y is oxycarbonyl, OC(O), whereas a thiourethane is formed where Y is thiocarbonyl, SC(O). A Y group is preferably a carbonyl group [C(O)].

Exemplary $C_1$–$C_{18}$ aliphatic (alkyl, alkenyl or alkynyl) groups present as $R^2$ substituent groups include straight and branched chain alkyl, alkenyl and alkynyl groups. Exemplary alkyl groups include methyl, ethyl, propyl, iso-propyl, butyl, isobutyl, t-butyl, pentyl, hexyl, octyl, nonyl, decyl, dodecyl, tetradecyl, hexadecyl and octadecyl. Exemplary alkenyl groups include ethylenyl, 2-propylenyl (allyl), 4-hexenyl and other monoethylenically unsaturated $C_2$–$C_{18}$ alkyl groups discussed above. Exemplary alkynyl groups include acetylenyl, 2-propylynyl, 5-hexynyl and the like alkynyl analogues of the above $C_2$–$C_{18}$ alkyl groups.

A $C_1$–$C_{18}$ hydrocarbyl that is an alkenyl or alkynyl group must be a $C_2$–$C_{18}$ group to permit the presence of the double or triple bond. $C_1$–$C_6$ alkyl groups are preferred, with methyl being particularly preferred.

An $R^2$ group can also be an aryl or substituted aryl group. Contemplated aryl groups are those that contain one aromatic six-membered ring or two fused aromatic six-membered rings and include hydrocarbyl groups such as phenyl and naphthyl, as well as 7hydrocarbyl groups bearing one or two nitrogen atoms that replace ring carbon atoms (mono- or diazahydrocarbyl). Exemplary aryl groups include pyridyl, pyrazinyl, pyrimidinyl, pyridazinyl, quinolinyl, isoquinoyl, quinoxalinyl, naphthyridinyl, phthalazinyl and quinazolinyl. Each of those aryl groups can be unsubstituted, or each can have a substituent selected from the group consisting of halo, trifluoromethyl, nitro, $C_1$–$C_6$ alkyl, $C_1$–$C_6$ alkoxy, amino, mono-$C_1$–$C_6$ alkylamino, di-$C_1$–$C_6$ alkylamino and $C_1$–$C_6$ alkylbenzylamino.

Exemplary phenyl $C_1$–$C_3$ alkylene groups include benzyl, phenethyl, and (β-methyl)phenethyl.

The above alkyl, alkenyl, unsubstituted and substituted aryl $R^2$ groups are well known in the art, and each can be bonded to the saccharide nitrogen atom using well known chemistry. The following discussion will therefore center upon aryl hydrocarbyl groups, phenyl and naphthyl, as being exemplary of the group, with the understanding that the other enumerated aryl and substituted aryl $R^2$ groups can be utilized with substantially similar chemistry.

Where $R^2$ is phenyl, benzoyl chloride or benzoic anhydride can be used to form a preferred amide bond. A benzenesulfonyl halide such as benzenesulfonyl chloride can similarly be used where Y is $SO_2$. Phenyl isocyanate is used where Y is HNC(O). A phenyl chloroformate is used where Y is OC(O), whereas a phenyl chlorothioformate is used where Y is SC(O).

Specifically contemplated substituted phenyl $R^2$ groups include those in which the substituent can be substituted at any position of the ring, with the meta and para positions being preferred. Mono-substituted $R^2$ phenyl groups are preferred over di-substituted groups.

Contemplated halo substituents include fluoro, chloro, bromo and iodo groups, with p-fluorophenyl, m-chlorophenyl, m-iodophenyl, p-bromophenyl and o-fluorophenyl being exemplary. Dihalo-substituted phenyl $R^2$ groups are also contemplated such as 3,4-dichlorophenyl, 3,5-dichlorophenyl, 2-chloro-4-fluorophenyl and 3-bromo-4-fluorophenyl.

Contemplated $C_1$–$C_6$ alkyl substituents of an $R^2$aryl group are the same as those discussed before. Methyl is preferred here. Exemplary, preferred $R^2$ groups include o-, m- and p-tolyl (methylphenyl) and p-t-butylphenyl groups as well as 3,4-dimethylphenyl and 3,5-dimethylphenyl groups.

Exemplary $C_1$–$C_6$ alkoxy groups are ethers containing a $C_1$–$C_6$ alkyl group. Methoxy is preferred here. Exemplary, preferred $R^1$ groups include o, m- and p-anisyl (methoxyphenyl), as well as 3,4-dimethoxyphenyl and 3,5-dimethoxyphenyl.

A nitrophenyl $R^2$ group is readily prepared by acylation using 3- or 4-nitrobenzoyl chloride. Acylation with 3,4- and 3,5-dinitrobenzoyl chloride provides the corresponding 3,4- and 3,5-dinitrophenyl $R^1$ groups. Amide formation using 3- or 4-trifluoromethylbenzoyl chloride similarly provides 3- or 4-trifluoromethylphenyl $R^2$ groups.

A substituted phenyl $R^2$ group can also contain an amino, mono-$C_1$–$C_6$ alkylamino, di-$C_1$–$C_6$ alkylamino, benzylamino or $C_1$–$C_6$ alkylbenzylamino substituent, wherein $C_1$–$C_6$ alkyl substituents are as discussed before.

Aminophenyl $R^2$ groups are most readily prepared from corresponding nitrophenyl $R^1$ groups discussed before by catalytic reduction of the nitro group after formation of the amide bond, as discussed before. Thus, for example, use of 3- or 4-nitrobenzoyl chloride to form the amide bond, upon reduction with palladium on carbon forms the corresponding 3- or 4-aminophenyl $R^2$ group. A similar use of 3,4- or 3,5-dinitrobenzoyl chloride provides the corresponding 3,4- or 3,5-diaminophenyl $R^2$ group after reduction.

Several di-$C_1$–$C_6$ alkylaminobenzoic acids such as 4-diethylaminobenzoic acid and 3- and 4-dimethylaminobenzoic acids can be purchased commercially and used to form an appropriate benzoyl halide or anhydride for forming an $R^2$-containing amide. The remaining di-$C_1$–$C_6$ alkylaminobenzoic acids and those compounds having two dialkylamino groups can be prepared using well known alkylation techniques from corresponding aminobenzoic acids or diaminobenzoic acids that are also commercially available.

A mono-$C_1$–$C_6$ alkylaminophenyl $R^2$ group can be prepared from the corresponding mono-$C_1$–$C_6$ alkylaminobenzoyl halide, whose remaining nitrogen valence is blocked by a readily removable blocking group such as t-Boc that can be removed with acid or a benzyl group that can be removed by hydrogenation, if desired, using palladium on carbon. Thus, acylation can take place using N-benzyl-N-propylaminobenzoyl chloride, with the N-benzyl group being removed by catalytic hydrogenation to provide the mono-$C_1$–$C_6$ alkylaminophenyl $R^2$ group. Of course, the benzyl group need not be removed, thereby providing a $C_1$–$C_6$ alkylbenzylamino group.

Each of the above-discussed phenyl or substituted phenyl substituents can be prepared by a well known amide-forming reaction. An exemplary reaction reacts an appropriate benzoyl halide or anhydride such as p-fluorobenzoyl chloride or benzoic anhydride with the unprotected amine group of an otherwise protected saccharide as is illustrated in detail hereinafter.

Both 1- and 2-naphthyl $R^2$ groups are contemplated, with 2-naphthyl being particularly preferred. These compounds can also be prepared using standard amide-forming technology as above, such as by reacting 2-naphthoyl chloride with an amine of an appropriate saccharide as discussed above.

It is to be understood that similar substituents are present on the aza- and diazahydrocarbyl aryl groups. For example, one can utilize any of the three pyridinecarboxyl chlorides, quinaldic acid chloride, 3-quinolinecarboxylic acid chloride, 2-quinoxaloyl chloride and the like to carry out an acylation reaction.

Similarly, where Y is $SO_2$, a corresponding sulfonyl halide is used. For example, one may utilize benzenesulfonyl chloride, toluenesulfonyl chloride, 8-quinolinesulfonyl chloride, 1- or 2-naphthalenesulfonyl chloride, and the like to form the sulfonamide.

Where Y is HNC(O), the isocyanate corresponding to a before-described carboxylic acid is a convenient reactant. Such derivatives can be readily prepared from the acid halide by reaction with azide, to form the acyl azide, which undergoes the Curtius rearrangement to form the isocyanate upon heating. Several contemplated isocyanates such as phenyl, ethyl, methyl, t-butyl and n-butyl isocyanates are commercially available.

Where Y is OC(O) or SC(O), a hydroxyl or mercapto substituted aryl $R^2$ group is reacted with phosgene to form the chloroformate or chlorothioformate that can be reacted with the saccharide amine to form the urethane or thiourethane linkage to an $R^2$. Several of these materials such as methyl, ethyl and phenyl chloroformates.

A phenyl $C_1$–$C_3$ alkylene $R^2$ group is a $C_1$–$C_3$ alkylene group that is itself substituted with a phenyl group, preferably at the terminal hydrocarbyl group carbon. This $R^2C(O)$ group thus contains a phenyl ring linked to a chain of 2–4 carbon atoms. Exemplary $C(O)R^2$ alkylene groups include 2-phenylacetoyl, 3-phenylpropionyl and 4-phenylbutanoyl [$\phi CH_2C(O)$, $\phi CH_2CH_2C(O)$ and $\phi(CH_2)_3C(O)$, respectively, where $\phi$=phenyl]. These compounds can be prepared by reaction of an appropriate acid halide or anhydride with a saccharidal amine as above. Catalytic reduction using hydrogen and a palladium on carbon catalyst can be used to form saturated alkylene groups from the unsaturated hydrocarbyl chains; saturated hydrocarbyl chains being preferred.

Each of the before-discussed $YR^2$ groups can be prepared by well known acylation reactions, as discussed before. The $YR^2$ group is usually introduced at a stage analogous to step e of Scheme 1, hereinafter. In an exemplary acylation, where Y is a preferred carbonyl group, an acid chloride or anhydride such as benzoyl chloride or p-fluorobenzoyl chloride or benzoic anhydride is reacted with the unprotected amine group of a saccharide, as is illustrated hereinafter, to form a peracylated compound analogous to Compound 12. Removal of the 0-linked acyl groups provides a compound analogous to Compound 13.

An X substituent group can be a $C_1$–$C_6$ acyloxy group; i.e., a $C_1$–$C_6$ acyl ester of a precursor hydroxyl group at that position, a $C_2$–$C_6$ hydroxylacyloxy group, a hydroxyl group, a halo group, as discussed previously, or an azido group. An X substituent is preferably hydroxyl. Exemplary $C_1$–$C_6$ acyl (hydrocarboyl) groups have already been discussed, and a $C_1$–$C_6$ acyloxy group is a $C_1$–$C_6$ acyl group that further includes an additional oxygen atom bonded to the carbonyl carbon atom of an acyl group. A $C_2$–$C_6$ hydroxylacyloxy group is an above-discussed $C_1$–$C_6$ acyloxy group that further includes a substituent hydroxyl group. Exemplary $C_2$–$C_6$ hydroxylacyloxy groups include hydroxyacetate, lactate, 3-hydroxybutyrate, 2-hydroxyisovalerate and 2-hydroxycaproate. An X substituent is usually other than $C_1$–$C_6$ acyloxy or $C_2$–$C_6$ hydroxylacyloxy unless both sialylation and fucosylation are carried out enzymatically, as is discussed hereinafter.

Syntheses of sialic acid derivatives containing an X substituent are disclosed in published international application WO 92/16640 that was published on Oct. 1, 1992. The use of those compounds for sialylating saccharides is also disclosed in that publication.

An $R^3$ group is methyl or hydroxymethyl, so that along with the depicted carbonyl group [C(O)] $R^3$ forms an N-acetyl or N-hydroxyacetyl group. Sialic acid derivatives containing either $R^3$ group can be used in an enzymatic sialylation as described herein.

$Z^1$ and $Z^2$ groups are preferably both α-L-fucosyl groups. However, $Z^1$ or $Z^2$, but not both, can also be hydrogen. It has been found that a contemplated bivalent inhibitor containing only one fucosyl group provides better cellular adhesion inhibition than does a standard compound such as $SLe^x$. However, bivalent inhibitors containing two α-L-fucosyl groups are typically still better inhibitors of cellular adhesion.

It is noted that the sialic acid portion of a compound of structural Formula I can be present in protonated form, or in a salt as the carboxylate as is shown in Scheme 2. When present as a carboxylate, the cation, M, is often not shown, but can be any pharmaceutically acceptable cation such as ammonium, sodium, potassium, calcium, magnesium, iron, aluminum or the like that forms a water-soluble or water-dispersible compound. Additional pharmaceutically acceptable anions such as chloride, bromide, acetate and the like can also be present to balance the valence of the cation, M.

Thus, whereas structural Formula I represents the general structure of a contemplated inhibitor, inhibitors in which one or the other of $Z^1$ and $Z^2$ is hydrogen, but not both, are hydrogen are also contemplated. Structural formulas for such compounds are illustrated herein below by structural Formulas II and III. The most preferred structure in which $Z^1$ and $Z^2$ are both α-L-fucosyl is also shown hereinbelow as a compound of structural Formula IV. The groups R, $R^2$, $R^3$ and X are as previously discussed. Structural formulas for preferred compounds in which Y is carbonyl are shown thereafter as structural Formulas IIA, IIIA and IVA, respectively.

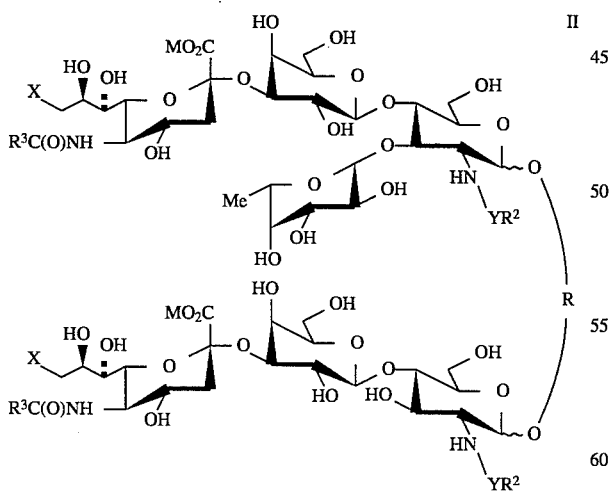

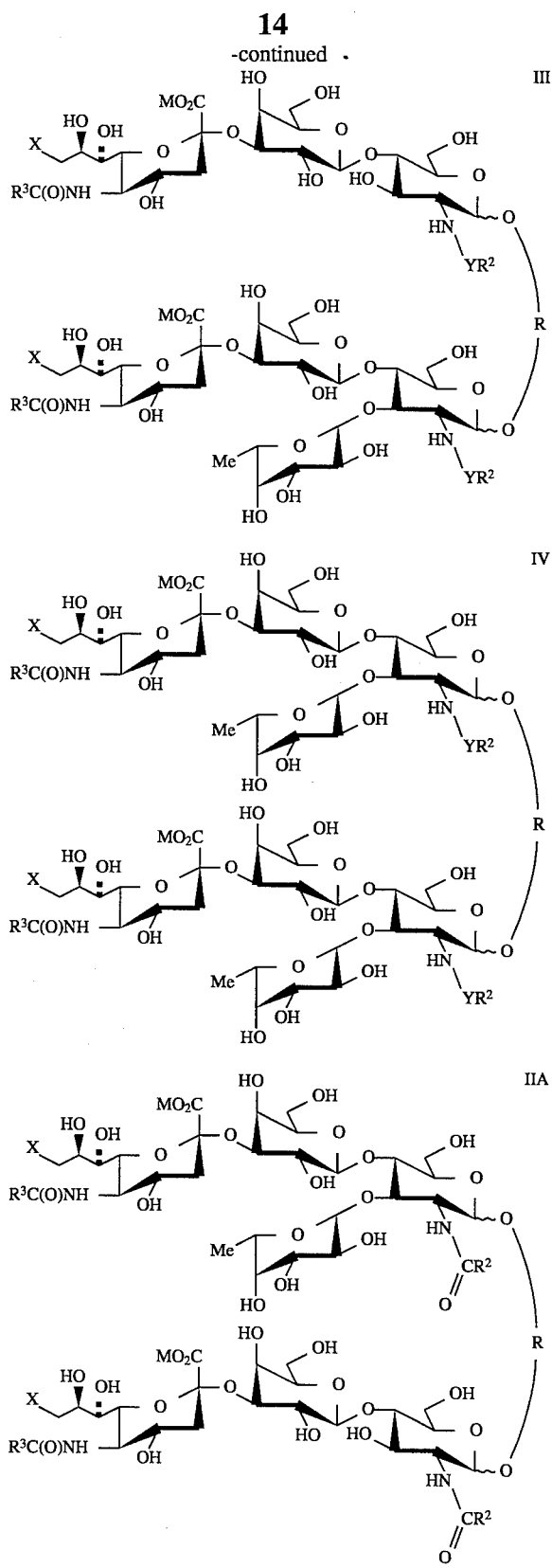

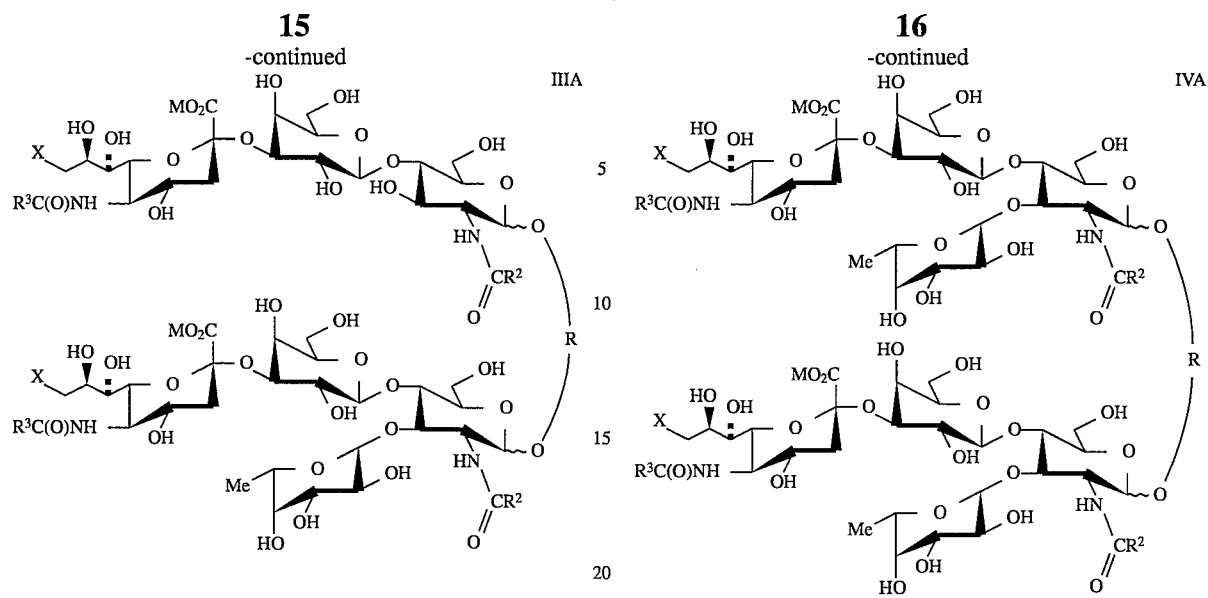
Exemplary bivalent SLe$^x$ saccharides corresponding to preferred Formulas IIA, IIIA and IVA are illustrated below along with their compound numbers.
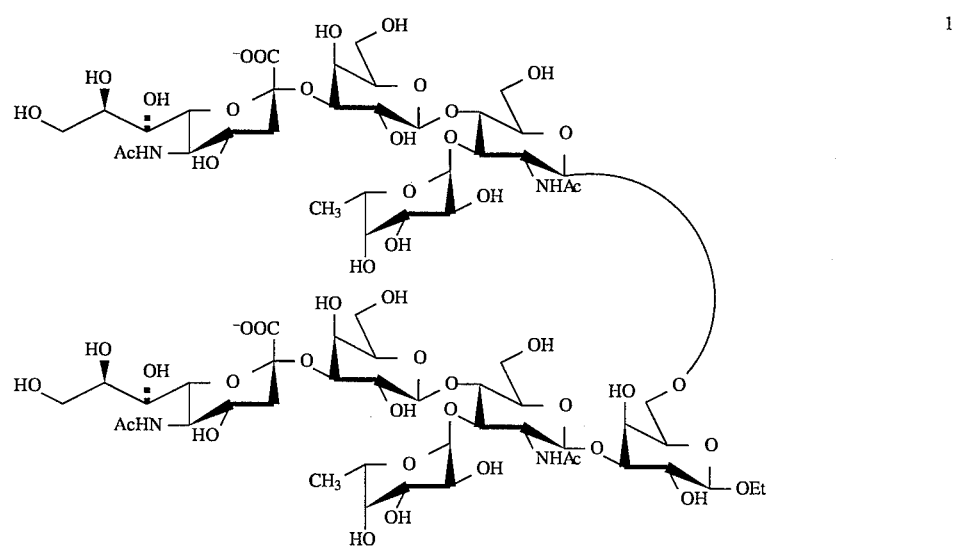

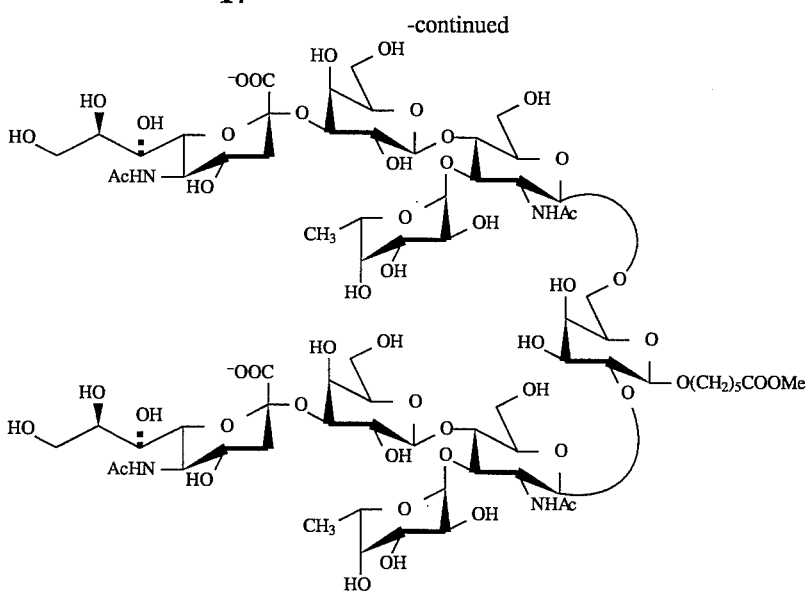
20
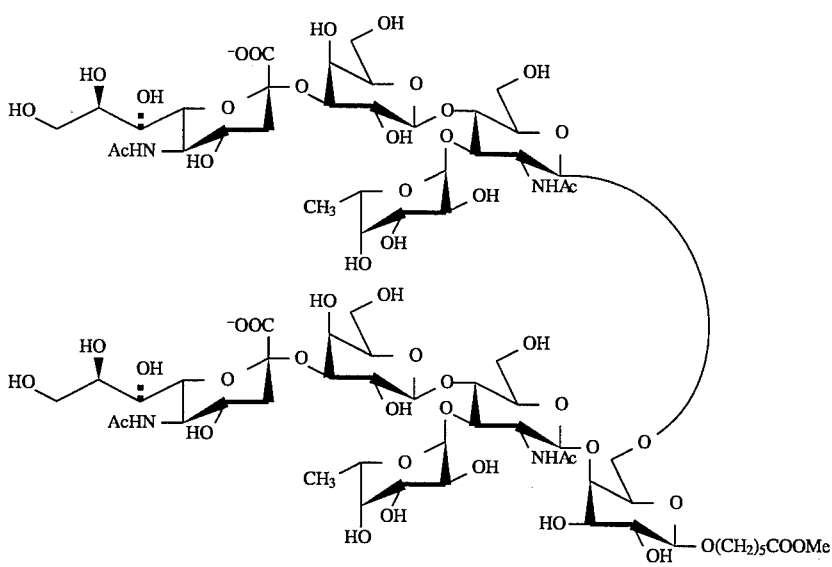
21
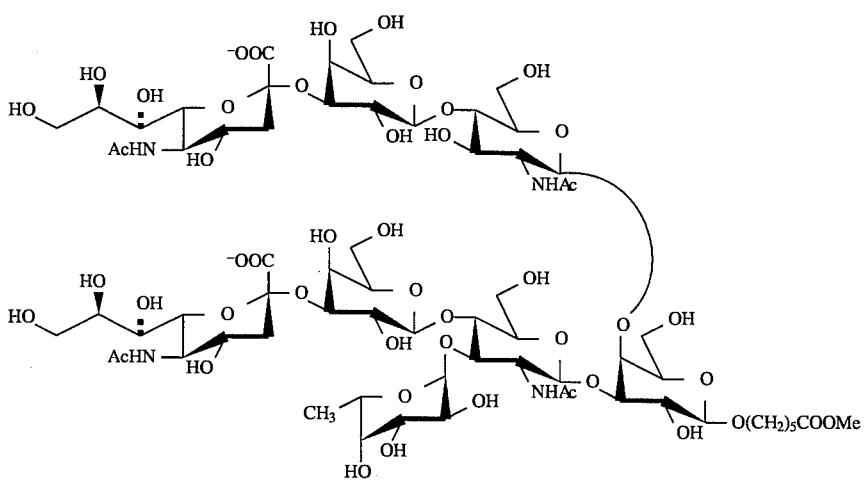
22

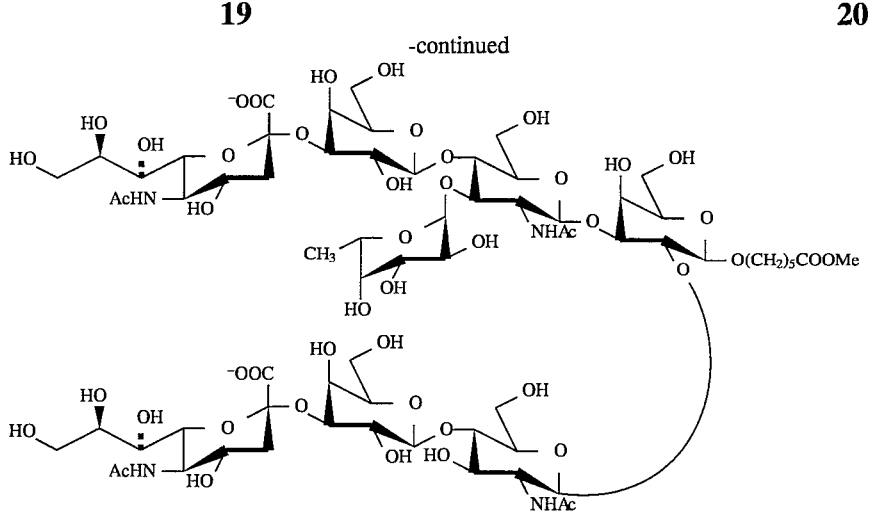

-continued

23

B. Compound Syntheses

Recent advances in enzymatic synthesis of oligosaccharides [Ichikawa et al., *J. Am. Chem. Soc.*, 114:9283 (1992); Ball et al., *J. Am. Chem. Soc.*, 114:5449 (1992); Palcic et al., *Carbohydr. Res.*, 190:1 (1989)] have permitted the synthesis of several bivalent SLe$^x$ galactosides of which Compound 1 is exemplary. Compound 1 is a compound modeled after a branched O-glycan in which SLe$^x$ is coupled via a 3- and 6-linkage to a galactoside.

The exemplary preparation of bivalent SLe$^x$ galactoside Compound I utilizes a combined chemical and enzymatic [Ichikawa et al., *J. Am. Chem. Soc.*, 114:9283 (1992); Ball et al., *J. Am. Chem. Soc.*, 114:5449 (1992); Palcic et al., *Carbohydr. Res.*, 190:1 (1989)] approach in which sialic acid and fucose are introduced enzymatically during the final two steps of the synthesis. Use of this combined methodology provides an efficient and economical means for preparing complex oligosaccharide structures that is amenable to modification for use in large scale.

The synthesis of Compound 1 is shown in Scheme 1, below, and began by conversion of protected galactoside alcohol Compound 6 into the disaccharide Compound 8 by reaction in step b with 2-deoxy-2-phthalimido-3,4,6-tri-O-acetyl-β-glucopyranosyl bromide [Lemieux et al., *ACS Symp. Ser.*, 39:90 (1976)] using silver trifluoromethylsulfonate (AgOTf) and collidine. Compound 6 was prepared in step a from Compound 5 using literature methods [Wallenfels et al., *Justus Liebigs Ann. Chem.*, 635:166 (1960); Lemieux et al., *Can. J. Chem.*, 60:68 (1981)] in step a. A before-discussed R$^1$ group is preferably added when a compound such as Compound 5 is prepared, as compared to adding the desired R$^1$ group at a stage later in the synthesis. The position of the 2-benzoate in Compound 6 was verified by adding trichloracetyl isocyanate to the NMR sample (CDCl$_3$) to form Compound 7. The spectrum contained a doublet of doublets at 4.27 ppm (J=8.0 and 2.3 Hz) typical of the H-3 of galactose. Deprotection in step c using 80 percent acetic acid in water and coupling of the recovered diol Compound 9 with 2-deoxy-2-phthalimido-3,4,6-tri-O-acetyl-β-glucopyranosyl bromide using AgOTf and collidine in step d afforded the trisaccharide Compound 10. [Lemieux et al., *ACS Symp. Ser.*, 39:90 (1976)].

The position of substitution was verified by reacting Compound 10 with trichloroacetyl-isocyanate in the NMR tube (CDCl$_3$) to produce Compound 11. A down field shift of a new peak to 5.39 ppm with two small coupling constants (J=2.1 Hz) was observed indicating that the 4-position proton of the ethyl galactoside was unsubstituted. Hydrazinolysis and acylation in step e provided Compound 10. Deacetylation of Compound 10 in step f using sodium methoxide in 25 percent methanol in water afforded the deblocked trisaccharide Compound 13. [Bundle et al., *Can. J. Chem.*, 57:662 (1979); Lemieux et al, *Can J. Chem.*, 69:76 (1982); Oltvoort et al., *Synthesis*, 305 (1981)], whose structure was confirmed by NMR. When a R$^2$ other than acetyl is utilized, that R$^2$ group can be introduced at this step (e) by replacing acetic anhydride with an appropriate R$^2$ anhydride or acid halide, pyrocarbonate (or chloroformate), sulfonyl chloride, isocyanate or chlorothioformate acylating reagent discussed before.

Scheme 1

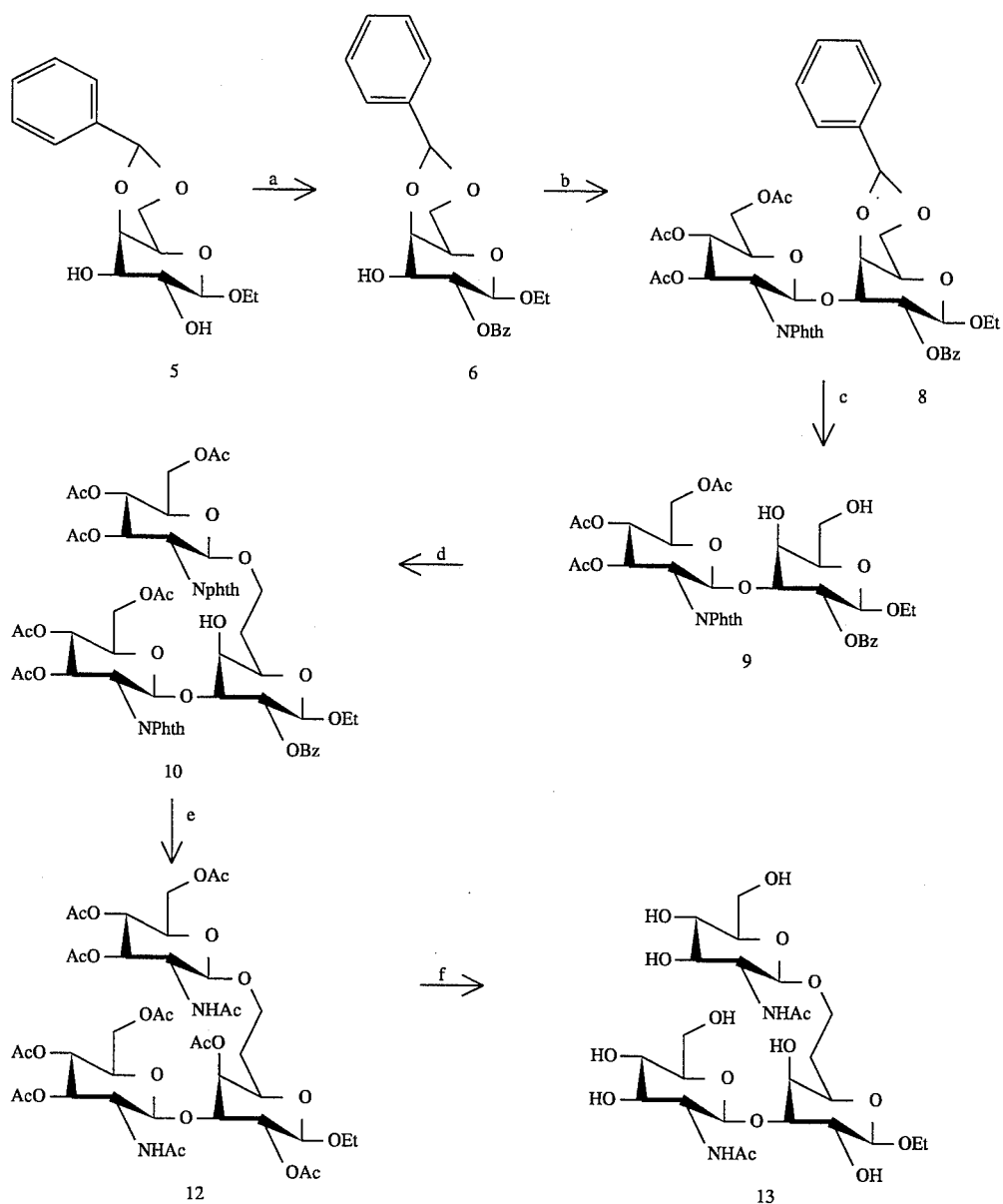

Scheme 2, below, illustrates the enzymatic synthetic steps of this exemplary synthesis. Thus, double enzymatic galactosylation [Moore et al., *J. Cell Biol.*, 118:445 (1992); Ichikawa et al., *J. Am. Chem. Soc.*, 114:9283 (1992); Ball et al., *J. Am. Chem. Soc.*, 114:5449 (1992); Palcic et al., *Carbohydr. Res.*, 190:1 (1989)] (EC 2.4.1.22 and EC 5.1.3.2) of Compound 13 furnished the pentasaccharide Compound 14 in step a. The transfer of sialic acid to produce Compound 15 in step b was catalyzed by N-type α(2,3)-sialyl transferase [Ichikawa et al., *J. Am. Chem. Soc.*, 114:9283 (1992)](EC 2.4.99.6) using a stoichiometric [Palcic et al., *Carbohydr. Res.*, 190:1 (1989)] amount of CMP-sialic acid to drive the reaction to completion (80 percent isolated yield). Monitoring of the reaction by TLC suggested that incorporation of the first sialic acid was rapid, but that addition of a second sialic acid proceeded slowly. Addition of alkaline phosphatase to hydrolyze the product phospho-ester CMP helps to drive the reaction to completion. Introduction of a sialic acid analogue of Formula I containing an X-substituent at the sialyl 9-position other than a hydroxyl group is also effected at this step, as discussed before.

Fucosylation of Compound 15 in step c catalyzed by fucosyl transferase V [Ichikawa et al., *J. Am. Chem. Soc.*, 114:9283 (1992)] using stoichiometric quantities of GDP-fucose afforded Compound 1 as the ammonium salt (84 percent isolated yield). The structure of Compound i was verified by 2D COESY NMR.

It has been found that enzymatic fucosylation of some analogues of Compound 15 having differently bonded R groups adds only one fucosyl group, resulting in compounds such as Compounds 22 and 23, above. Those compounds were nevertheless good inhibitors whose ability to inhibit cell adhesion was more than twice that of SLe$^x$ itself on a molar basis.

Scheme 2

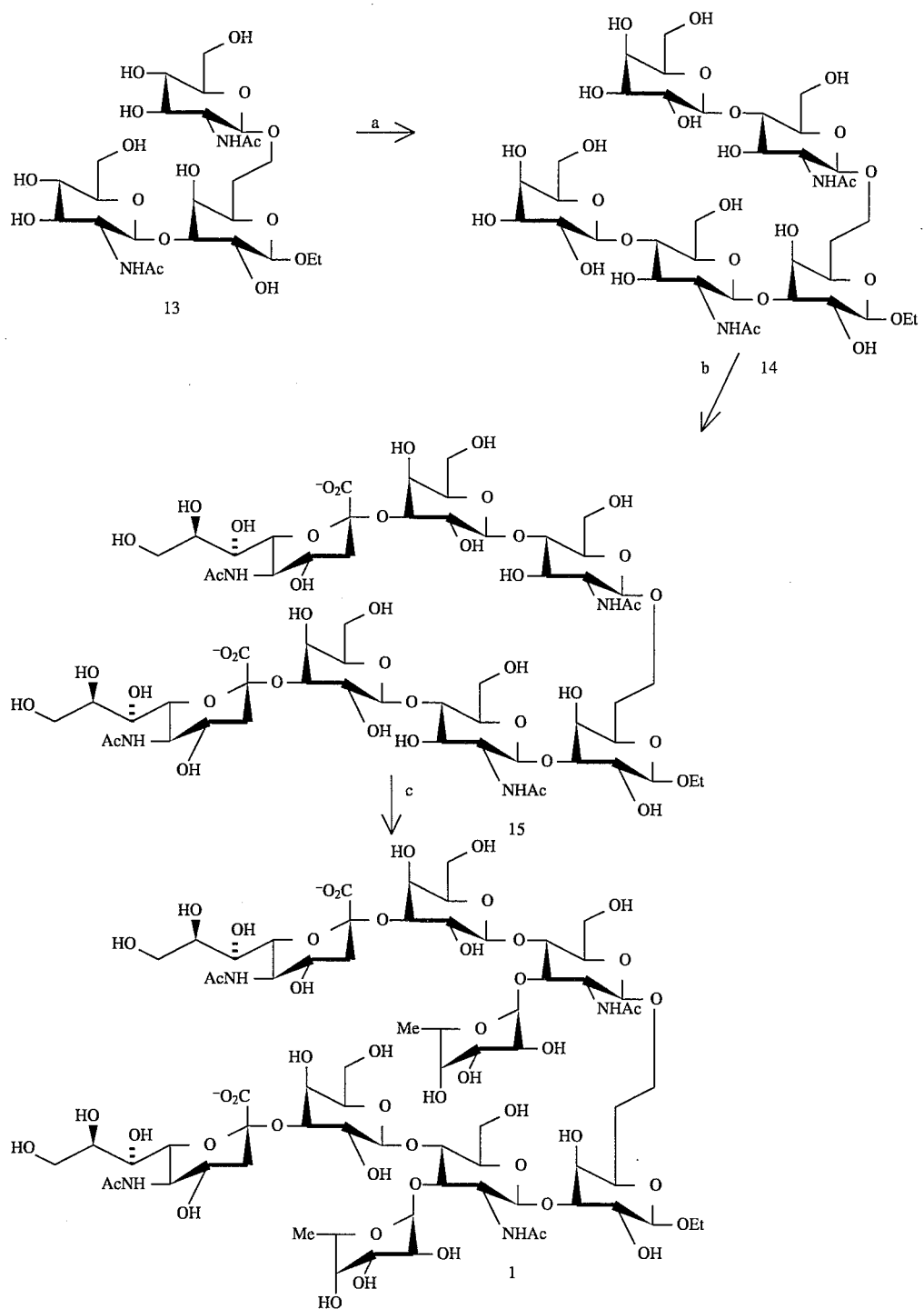

It should be understood that the method of syntheses illustrated in Schemes 1 and 2 is not the only way to prepare Compound 1 or another contemplated compound. For example, a pentasaccharide Compound 16 can be prepared by reaction of N-phthalimido peracetyl lactosamine d chloride (Compound 17) with Compound 6, as shown in Scheme 3, below. Compound 17 can itself be prepared from lactosamine by reaction with phthalic anhydride, followed by acylation with acetic anhydride and then reaction of the resulting phthalimido peracetyl compound with aluminum chloride in dichloromethane. Steps b through f of Scheme 1 are then followed to prepare Compound 16. The $R^2$ group of Compound 16 is shown generically and is added to the deacylated intermediate at step e after hydrazinolysis to remove the phthalimido (Phth) and acetyl (Ac) groups. The sodium methoxide treatment of step f removes the esters that are made when the nitrogen atom is acylated. Compound 16 can thereafter be sialylated and fucosylated as discussed in Scheme 2.
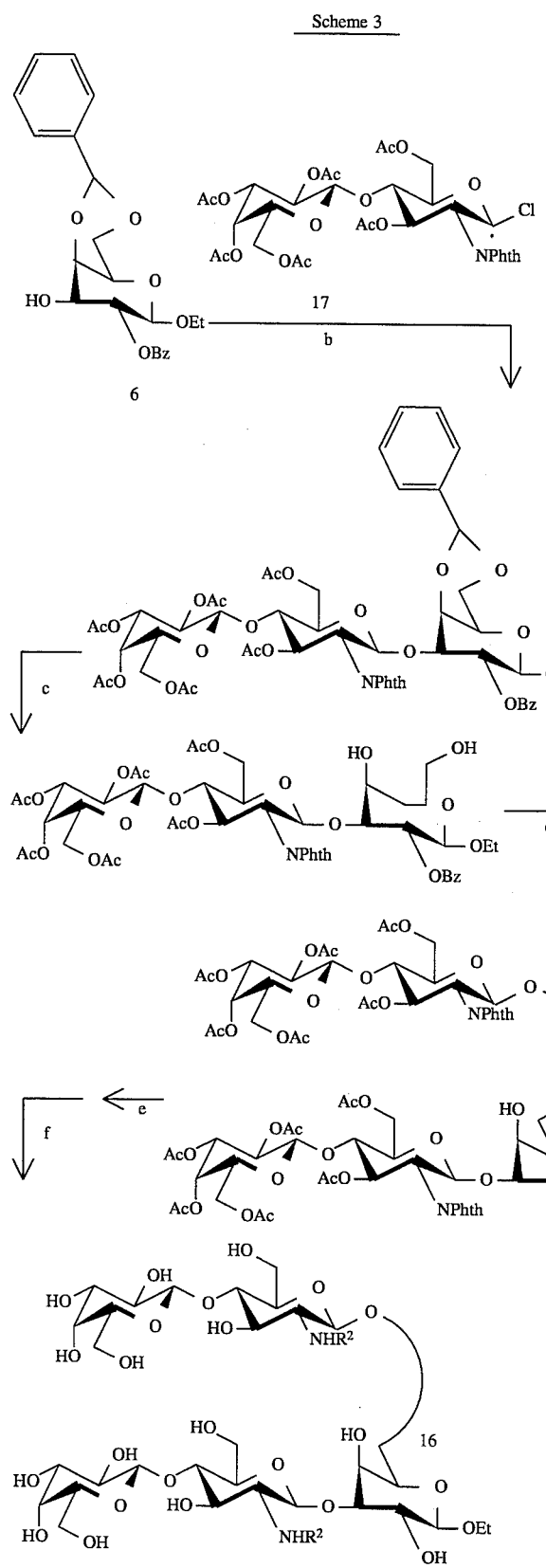
Scheme 3

Sialylation and fucosylation can also be carried out by non-enzymatic, organic chemical means, although sialylation is preferably carried out enzymatically. Where fucosylation is carried out by organic chemical reactions, the hydroxyls and carboxyl groups of disialylated compounds are first blocked. This blocking step is readily carried out by extensive reaction with acetic anhydride, which forms acetate groups on all but one of the available hydroxyls and a lactone between the sialyl carboxyl and a hydroxyl group. The lactone is reacted with a $C_1$–$C_6$ alcohol such as methanol to form an acylated hydroxy ester, whose remaining hydroxyl is then acylated as with acetic anhydride.

Reaction of the acylated diester with glacial acetic acid in methanol:water selectively transfers the acetyl group from the 3-position to the 2-amino substituent of the glucosamide unit, providing a free hydroxyl group for glycosyl bond formation with a fucose unit. Fucosylation can then be carried out using tri-O-benzyl fucosyl fluoride in dichloroethane as solvent in the presence of 4 Å molecular sieves, tetramethyl urea, $SnCl_2$ and $AgClO_4$. The benzyl groups can then be removed from the fucosylated product by hydrogenolysis, and the acetyl groups and methyl ester removed by reaction with methoxide ion in methanol/water to provide a deblocked bivalent compound of Formula I.

It is noted that when sialylation and/or fucosylation are carried out by other than enzymatic means, X substituents that are $C_1$–$C_6$ acyloxy and $C_2$–$C_6$ hydroxyacyloxy can be lost during various protection (blocking) and deprotection (deblocking) steps in the synthesis. Thus, X substituents that are hydroxyl, halo and azido are preferred, with hydroxyl being particularly preferred.

C. Cell Adhesion Inhibition Assay Methods

Numerous direct and indirect methods for in vitro screening of inhibitors of ligand-receptor interactions are available and known to those skilled in the art. For instance, the ability to inhibit adhesion of $SLe^x$-bearing cells to cells expressing a particular selectin can be determined.

As discussed before, several selectin receptor genes have been cloned, and thus, the genes can be inserted and expressed in a wide variety of cells, such as COS cells, CHO cells, adenovirus-transformed human kidney cells as used herein, and the like so that a recombinant selectin receptor such as rELAM (recombinant ELAM-1 or sol-E-selectin) can be used in assays when bound to a solid support such as a plastic microtiter plate well, as is described hereinafter. This expressed recombinant is soluble in aqueous media, contains the 527 amino-terminal amino acid residues, and lacks the transmembrane domain of the native molecule.

The use of an above recombinant is preferred for assaying inhibition of cellular adhesion (binding). The use of a substantially similar assay had been reported to correlate well with results using cells that express the E-selectin receptor [Lobb et al., *J. Immunol.*, 147:124–129 (1991)].

In addition, cells that do not normally express $SLe^x$ are capable of being transformed with one or more glycosyltransferase genes that confer on the transformed cells the ability to synthesize the ligand. [See, e.g., Lowe et al., *Cell*, 63:475–484 (1990)]. In some assays, the inhibitor compound or agent is incubated with labeled $SLe^x$-bearing cells and activated cells expressing cell surface selectins or recombinant selectin immobilized on a solid surface. Inhibition of cellular adhesion can then be determined by detecting label bound to the surface after appropriate washes.

Typically, the in vitro assays of a contemplated bivalent $SLe^x$ saccharide compound are competition assays that detect the ability of a contemplated compound to competitively inhibit binding of selectin to cells expressing $SLe^x$ on their surfaces. The use of the before-discussed sol-E-selectin is preferred in these competition assays, although selectin-expressing cells can also be used. Selectin-expressing cells are typically activated platelets or activated endothelial cells with a recombinant selectin being as useful, whereas the $SLe^x$-bearing cells are usually neutrophils or HL-60 cells.

A contemplated bivalent $SLe^x$ saccharide inhibits the in vitro binding of $SLe^x$-bearing cells such as HL-60 cells to solid phase-bound sol-E-selectin by more than twice as much as does an equimolar amount of $SLe^x$ itself. Put differently, the ratio of the $IC_{50}$ value of $SLe^x$ to the $IC_{50}$ value of a contemplated bivalent $SLe^x$ saccharide is greater than two in such an in vitro assay. Thus, a contemplated bivalent $SLe^x$ saccharide exhibits an $IC_{50}$ value in the in vitro assay that is less than one-half that exhibited by $SLe^x$. That ratio is preferably about three to about 100. Details for an in vitro assay using sol-E-selectin are also provided hereinafter.

Other assay formats involve detection of the presence or absence of various physiological changes in either $SLe^x$ ligand-bearing or selectin-bearing cells that result from the interaction. Examples of suitable assays include the measurement of changes in transcription activity induced by binding (see, e.g., PCT publication No. 3712820), the detection of various cell mediated extra-cellular effects (see, e.g., PCT Publication No. 90/00503), and the detection of changes in the membrane potential of individual cells (see, e.g., U.S. Pat. No. 4,343,782), all of which are incorporated herein by reference. Alternatively, conformational changes in isolated receptors or ligands can be detected; see, e.g., U.S. Pat. No. 4,859,609, which is incorporated herein by reference. Still further, one can bind $SLe^x$-expressing cells to solid support-bound selectin, lyse the bound cells and assay for a protein that could only have been present in the bound cells.

Any component of the assay, including the ligand, the selectin receptor, or the bivalent $SLe^x$ saccharide compound, can be bound to a solid surface. Many methods for immobilizing biomolecules on solid surfaces are known in the art. For instance, the solid surface can be a membrane (e.g., nitrocellulose), a microtiter dish (e.g., PVC or polystyrene) or a bead. The desired component can be covalently bound or non-covalently attached through unspecific bonding.

A wide variety of organic and inorganic polymers, both natural and synthetic can be employed as the material for the solid surface. Illustrative polymers include polyethylene, polypropylene, poly (4-methylbutene), polystyrene, polymethacrylate, poly(ethylene terephthalate), rayon, nylon, poly(vinyl butyrate), silicones, polyformaldehyde, cellulose, cellulose acetate, nitrocellulose, etc. Other materials that can be employed include paper, glasses, ceramics, metals, metalloids, semiconductive materials, cermets or the like. In addition are included substances that form gels, such as proteins, e.g., gelatins, lipopolysaccharides, silicates, agarose and polyacrylamides or polymers which form several aqueous phases, such as dextrans, polyalkylene glycols (alkylene of 2 to 3 carbon atoms) or surfactants, e.g., amphiphilic compounds, such as phospholipids, long chain (12–24 carbon atoms) alkyl ammonium salts and the like. Where the solid surface is porous, various pore sizes may be employed depending upon the nature of the system.

In preparing the surface, a plurality of different materials can be employed, particularly as laminates, to obtain various properties. For example, protein coatings, such as gelatin can be employed to avoid non-specific binding, simplify covalent conjugation, enhance signal detection or the like.

If covalent bonding between a compound and the surface is desired, the surface is usually polyfunctional or capable of being polyfunctionalized. Functional groups that can be present on the surface and used for linking can include carboxylic acids, aldehydes, amino groups, cyano groups, ethyleneic groups, hydroxyl groups, mercapto groups and the like. The manner of linking a wide variety of compounds to various surfaces is well known and is amply illustrated in the literature. See for example Immobilized Enzymes, Inchiro Chibata, Halsted Press, New York (1978), and Cuatrecasas, *J. Biol. Chem.*, 245;3059 (1970) which is incorporated herein by reference.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A binds a carbohydrate containing compound but not a labelled protein that lacks glycosylation. Various solid surfaces for use in noncovalent attachment of assay components are reviewed in U.S. Pat. Nos. 4,447,576 and 4,254,082, which are incorporated herein by reference.

The label mentioned before can be coupled directly or indirectly to the desired component of the assay according to methods well known in the art, or can be a protein endogenous to the bound cells. A wide variety of labels can be used. The component can be labeled by any one of several methods. The most common method of detection is the use of autoradiography with $^3$H, $^{125}$I, $^{35}$S, $^{14}$C, or $^{32}$P labeled compounds or the like. The choice of radioactive isotope depends on research preferences due to ease of synthesis, varying stability, and half lives of the selected isotopes. Other non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation.

Non-radioactive labels are often attached by indirect means. Generally, a ligand molecule (e.g., biotin) is covalently bound to the molecule. The ligand then binds to an anti-ligand (e.g., streptavidin) molecule that is either inherently detectable or covalently bound to a signal system, such as a detectable enzyme, a fluorescent compound, or a chemiluminescent compound. Ligands and antiligands can be varied widely. Where a ligand has a natural antiligand, for example, biotin, thyroxine, and cortisol, it can be used in conjunction with the labeled, naturally occurring antiligands. Alternatively, any haptenic or antigenic compound can be used in combination with an antibody.

The before-mentioned label can also be an enzyme or other protein present in a cell whose adhesion is to be inhibited. The amount of that enzyme can thereby be used as a label to determine the amount of binding. Myeloperoxidase is one such protein present in HL-60 cells that is useful as a label in the binding inhibition studies discussed hereinafter.

The bivalent SLe$^x$ saccharide molecules can also be conjugated directly to signal generating compounds, e.g., by conjugation with an enzyme or fluorophore via an amidified carboxyl of a $C_1$–$C_6$ alkyl $C_1$–$C_5$ alkylene ω-carboxylate $R^l$ group. Enzymes of interest as labels are primarily hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various signal producing systems which may be used, see, U.S. Pat. No. 4,391,904, which is incorporated herein by reference.

D. Pharmaceutical Compositions

A pharmaceutical composition comprising a before-discussed bivalent SLe$^x$ saccharide dissolved or dispersed in a pharmaceutically acceptable diluent or carrier is also contemplated. Such a pharmaceutical composition contains a bivalent SLe$^x$ saccharide compound present in a cellular adhesion-inhibiting amount.

As will be seen from the following disclosure, a cellular adhesion-inhibiting amount can vary widely. That amount is, however, sufficient to inhibit binding of cells that express sialyl Le X on their cell surfaces to selectin, particularly E-selectin (ELAM-1) preferably by about one-half or more. An exemplary cellular adhesion-inhibiting amount is about 5 to about 60 mg/kg.

A contemplated pharmaceutical composition can be used to block or inhibit cellular adhesion associated with a number of disorders. For instance, a number of inflammatory disorders are associated with selectins expressed on vascular endothelial cells and platelets. The term "inflammation" is used here to refer to reactions of both the specific and non-specific defense systems. A specific defense system reaction is a specific immune system reaction to an antigen. Exemplary of specific defense system reactions include antibody response to antigens, such as viruses, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of peripheral mononuclear (PMN) leukocytes at sites of bacterial infection (e.g., pulmonary infiltrates in bacterial pneumonia and pus formation in abscesses).

Other treatable disorders include, e.g., rheumatoid arthritis, post-ischemic leukocyte-mediated tissue damage (reperfusion injury), frost-bite injury or shock, acute leukocyte-mediated lung injury (e.g., adult respiratory distress syndrome), asthma,.traumatic shock, septic shock, nephritis, and acute and chronic inflammation, including atopic dermatitis, psoriasis, and inflammatory bowel disease. Various platelet-mediated pathologies such as atherosclerosis and clotting can also be treated. In addition, tumor metastasis can be inhibited or prevented by inhibiting the adhesion of circulating cancer cells. Examples include carcinoma of the colon and melanoma.

By way of example, reperfusion injury is particularly amenable to treatment by a contemplated pharmaceutical composition. A composition that inhibits a GMP-140 selectin-ligand interaction can be particularly useful for treating or preventing reperfusion injury. A contemplated pharmaceutical composition can be used prophylactically prior to heart surgery to enhance postsurgical recovery.

Because GMP-140 is stored in Weibel-Palade bodies of platelets and endothelial cells and is released upon activation by thrombin to mediate adhesion of neutrophils and monocytes, inhibitors of the GMP-140 ligand interaction can be especially useful in minimizing tissue damage that often accompanies thrombotic disorders. For instance, such inhibitors can be of therapeutic value in patients who have recently experienced stroke, myocardial infarctions, deep vein thrombosis, pulmonary embolism, etc. The compounds are especially useful in pre-thrombolytic therapy.

A contemplated composition finds particular use in treating the secondary effects of septic shock or disseminated intravascular coagulation (DIC). Leukocyte emigration into tissues during septic shock or DIC often results in pathological tissue destruction. Furthermore, these patients can have widespread microcirculatory thrombi and diffuse inflammation. A therapeutic composition provided herein inhibits leukocyte emigration at these sites and mitigates tissue damage.

An inhibitor of selectin-ligand interaction is also useful in treating traumatic shock and acute tissue injury associated therewith. Because the selectins play a role in recruitment of leukocytes to the sites of injury, particularly ELAM-1 in cases of acute injury and inflammation, inhibitors thereof can be administered locally or systemically to control tissue damage associated with such injuries. Moreover, because of the specificity of such inhibitors for sites of inflammation, e.g., where ELAM-1 receptors are expressed, these compositions can be more effective and less likely to cause complications when compared to traditional anti-inflammatory agents.

Thus, the present invention also provides a pharmaceutical composition that can be used in treating the aforementioned conditions. A contemplated pharmaceutical composition is comprised of a before-described bivalent $SLe^x$ saccharide compound that inhibits the interaction between the $SLe^x$ ligand and selectin receptors, the bivalent $SLe^x$ saccharide compound being dissolved or dispersed in a pharmaceutically acceptable diluent. A contemplated pharmaceutical composition is suitable for use in a variety of drug delivery systems. For a brief review of present methods for drug delivery, see, Langer, *Science*, 249.:1527–1533 (1990).

In light of the complexity of the inflammatory response in mammals, one of skill will readily recognize that a contemplated pharmaceutical composition can further include other compounds known to interfere with the function of other cellular adhesion molecules. For instance, members of the integrin family of adhesion molecules are thought to play a role in the extravasation of leukocytes at points of infection. For a review of intercellular adhesion receptors, including selectin receptors, and their role immune function, see Springer, *Nature*, 346.:425–434 (1990). In addition, successful treatment using a contemplated pharmaceutical composition can also be determined by the state of development of the condition to be treated. Because different adhesion molecules can be up or down regulated in response to a variety of factors during the course of the disease or condition, one of skill will recognize that different pharmaceutical compositions can be required for treatment of different inflammatory states.

In another embodiment, a before-described bivalent $SLe^x$ saccharide of the pharmaceutical composition can be used to target conventional anti-inflammatory drugs or other agents to specific sites of tissue injury. By using such a compound to target a drug to a selectin receptor on, e.g., a vascular endothelial cell, such drugs can achieve higher concentrations at sites of injury. Side effects from the conventional anti-inflammatory chemotherapeutic agents can be substantially alleviated by the lower dosages, the localization of the agent at the injury sites and/or the encapsulation of the agent prior to delivery.

The targeting component, i.e., the bivalent $SLe^x$ saccharide that binds to a selectin, can be directly or indirectly coupled to the chemotherapeutic agent. The coupling, which can be performed by means, generally known in the art, should not substantially inhibit the ability of the ligand to bind the receptor nor should it substantially reduce the activity of the chemotherapeutic agent. A variety of chemotherapeutics can be coupled for targeting. For example, anti-inflammatory agents that can be coupled include immunomodulators, platelet activating factor (PAF) antagonists, cyclooxygenase inhibitors, lipoxygenase inhibitors, and leukotriene antagonists. Some preferred moieties include cyclosporin A, indomethacin, naproxen, FK-506, mycophenolic acid, etc. Similarly, antioxidants, e.g., superoxide dismutase, are useful in treating reperfusion injury when targeted by a contemplated saccharide compound. Likewise, anticancer agents can be targeted by coupling the bivalent $SLe^x$ saccharide to the chemotherapeutic agent. Examples of agents that can be coupled include daunomycin, doxorubicin, vinblastine, bleomycin, etc. Here, again, a $C_1$–$C_6$ alkyl $C_1$–$C_5$ alkylene ω-carboxylate $R^1$ group can be used for coupling.

The selectin receptor targeting can also be accomplished via amphipaths, or dual character molecules (polar:nonpolar) that exist as aggregates in aqueous solution. Amphipaths include nonpolar lipids, polar lipids, mono- and diglycerides, sulfatides, lysolecithin, phospholipids, saponin, bile acids and salts. These molecules can exist as emulsions and foams, micelles, insoluble monolayers, liquid crystals, phospholipid dispersions and lamellar layers. These are generically referred to herein as liposomes. In these preparations the drug to be delivered is incorporated as part of a liposome in conjunction with a bivalent $SLe^x$ saccharide that binds to the selectin receptor.

A contemplated bivalent $SLe^x$ saccharide compound whose $R^1$ group is a $C_{12}$–$C_{18}$ hydrocarbyl group is particularly useful in such liposome preparations. Thus, liposomes filled with a desired chemotherapeutic agent can be directed to a site of tissue injury by the selectin-bivalent $SLe^x$ saccharide interaction. When the liposomes are brought into proximity of the affected cells, they deliver the selected therapeutic compositions.

The liposomes of the present invention are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream.

Typically, the major lipid component in the liposomes is phosphatidylcholine, phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Methods used in sizing and filter-sterilizing liposomes are discussed below. The acyl chain composition of phospholipid can also affect the stability of liposomes in the blood. One preferred phosphatidylcholine is partially hydrogenated egg phosphatidylcholine.

Targeting of liposomes using a variety of targeting agents (e.g., ligands, receptors and monoclonal antibodies) is well known in the art. (See, e.g., U.S. Pat. Nos. 4,957,773 and 4,603,044, both of which are incorporated herein by reference). Glycoproteins and glycolipids of a variety of molecular weights can be used as targeting agents. Typically, glycoproteins having a molecular weight less than about 300,000 daltons, preferably between about 40,000 and about 250,000 are used, more preferably between about 75,000 and about 150,000. Glycolipids of molecular weight of less than about 10,000 daltons, preferably between about 600 and about 4,000 are used.

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid derivatized bleomycin, in addition to using a bivalent $SLe^x$ saccharide for such coupling.

Targeting mechanisms generally require that the targeting agents be positioned on the surface of the liposome in such a manner that the target agents are available for interaction with the selectin receptor. The liposome is typically fashioned in such a way that a connector portion is first incorporated into the membrane at the time of forming the membrane. The connector portion must have a lipophilic portion that is firmly embedded and anchored in the membrane. It must also have a hydrophilic portion which is chemically available on the aqueous surface of the liposome. The hydrophilic portion is selected so that it will be chemically suitable to form a stable chemical bond with the targeting agent which is added later. Therefore, the connector molecule must have both a lipophilic anchor and a hydrophilic reactive group suitable for reacting with the target agent and holding the target agent in its correct position, extended out from the liposome's surface. In some cases it is possible to attach the target agent to the connector molecule directly, but in most instances it is more suitable to use a third molecule to act as a chemical bridge, thus linking the connector molecule which is in the membrane with the target agent which is extended, three dimensionally, off the vesicle surface.

Liposome charge is an important determinant in liposome clearance from the blood, with negatively charged liposomes being taken up more rapidly by the reticuloendothelial system [Juliano, *Biochem. Biophys. Res. Commun.*, 63:651 (1975)] and thus having shorter half-lives in the bloodstream. Liposomes with prolonged circulation half-lives are typically desirable for therapeutic and diagnostic uses. Liposomes which can be maintained from 8, 12, or up to 24 hours in the bloodstream provide sustained release of the selectin-ligand inhibitors of the invention, or can facilitate targeting of the inhibitors (which can be labeled to provide for in vivo diagnostic imaging) to a desired site before being removed by the reticuloendothelial system.

Typically, the liposomes are prepared with about 5–15 mole percent negatively charged phospholipids, such as phosphatidylglycerol, phosphatidylserine or phosphatidylinositol. Added negatively charged phospholipids, such as phosphatidylglycerol, also serves to prevent spontaneous liposome aggregating, and thus minimize the risk of undersized liposomal aggregate formation. Membrane-rigidifying agents, such as sphingomyelin or a saturated neutral phospholipid, at a concentration of at least about 50 mole percent, and 5–15 mole percent of monosialylganglioside, may provide increased circulation of the liposome preparation in the bloodstream, as generally described in U.S. Pat. No. 4,837,028, incorporated herein by reference.

Additionally, the liposome suspension can include lipid-protective agents that protect lipids and drug components against free-radical and lipid-peroxidative damages on storage. Lipophilic free-radical quenchers, such as alphatocopherol and water-soluble iron-specific chelators, such as ferrioxianine, are preferred.

Several methods are available for preparing liposomes, as described in, e.g., Szoka et al., *Ann. Rev. Biophys. Bioeng*, 9:467 (1980), U.S. Pat. Nos. 4,235,871, 4,501,728 and 4,837,028, incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture that is in a more easily hydrated powder-like form. This film is covered with an aqueous solution of the targeted drug and the targeting component and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

The hydration medium contains the targeted drug at a concentration that is desired in the interior volume of the liposomes in the final liposome suspension. Typically the drug solution contains between 10–100 mg/mL in a buffered saline. The concentration of the targeting SLX molecule or mimetic which binds a selectin is generally between about 0.1–20 mg/mL.

Following liposome preparation, the liposomes can be sized to achieve a desired size range and relatively narrow distribution of liposome sizes. One preferred size range is about 0.2–0.4 microns, which allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes can be extruded through successively smaller-pore membranes, to achieve a gradual reduction in liposome size.

Even under the most efficient encapsulation methods, the initial sized liposome suspension can contain up to 50 percent or more drug and targeting agent in free (non-encapsulated) form. Therefore, to maximize the advantages of liposomal targeted drug, it is important to remove free drug and targeting agent from the final injectable suspension.

Several methods are available for removing non-entrapped compound from a liposome suspension. In one method, the liposomes in the suspension are pelleted by high-speed centrifugation leaving free compound and very small liposomes in the supernatant. Another method involves concentrating the suspension by ultrafiltration, then resuspending the concentrated liposomes in a drug-free replacement medium. Alternatively, gel filtration can be used to separate large liposome particles from solute molecules.

Following treatment to remove free drug and/or targeting agent, the liposome suspension is brought to a desired concentration for use in intravenous administration. This can involve resuspending the liposomes in a suitable volume of injection medium, where the liposomes have been concentrated, for example by centrifugation or ultrafiltration, or concentrating the suspension, where the drug removal step has increased total suspension volume. The suspension is then sterilized by filtration as described above. The liposome-ligand preparation may be administered parenterally or locally in a dose which varies according to., e.g., the manner of administration, the drug being delivered, the particular disease being treated, etc.

For a pharmaceutical composition that comprises a bivalent $SLe^x$ saccharide compound that binds to selectin receptors, the dose of the compound can vary according to, e.g., the particular compound, the manner of administration, the particular disease being treated and its severity, the overall health and condition of the patient, and the judgment of the prescribing physician. For example, for the treatment of reperfusion injury, the dose is in the range of about 50 μg to 2,000 mg/day for a 70 kg patient. Ideally, therapeutic administration should begin as soon as possible after the myocardial infarction or other injury. A pharmaceutical composition is intended for parenteral, topical, oral or local administration, such as by aerosol or transdermally, for prophylactic and/or therapeutic treatment. A pharmaceutical composition can be administered in a variety of unit dosage forms depending upon the method of administration. For example, unit dosage forms suitable for oral administration include powder, tablets, pills, capsules and dragees.

Preferably, a pharmaceutical composition is administered intravenously. Thus, a pharmaceutical composition is provided for intravenous administration that comprises a solution of the bivalent $SLe^x$ saccharide compound dissolved or dispersed in a pharmaceutically acceptable diluent (carrier), preferably an aqueous carrier. A variety of aqueous carriers can be used, e.g., water, buffered water, 0.4 percent saline, and the like. These compositions can be sterilized by conventional, well known sterilization techniques, or can be sterile filtered. The resulting aqueous solutions can be packaged for use as is, or lyophilized, the lyophilized preparation being combined with a sterile aqueous solution prior to administration. A composition can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of bivalent $SLe^x$ saccharide compound utilized in a pharmaceutical composition is usually at or at least about 1 percent to as much as 10 to 30 percent by weight and is selected primarily by fluid volumes, viscosities, etc., in accordance with the particular mode of administration selected. As described above, the composition components can be delivered via liposome preparations.

Thus, a typical pharmaceutical composition for intravenous infusion can be made up to contain 250 mL of sterile Ringer's solution, and 25 mg of the bivalent $SLe^x$ saccharide compound. Actual methods for preparing parenterally administrable compounds are known or apparent to those skilled in the art and are described in more detail in for example, *Remington's Pharmaceutical Sciences,* 17th ed., Mack Publishing Company, Easton, Pa. (1985), which is incorporated herein by reference.

For solid compositions, conventional nontoxic solid diluents (carriers) may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95 percent of active ingredient, that is, a before-described bivalent $SLe^x$ saccharide compound, preferably about 20 percent (see, Remington's, supra).

For aerosol administration, a bivalent $SLe^x$ saccharide compound is preferably supplied in finely divided form along with a surfactant and propellant. Typical percentages of a bivalent $SLe^x$ saccharide compound are about 0.5 to about 30 percent by weight, and preferably about 1 to about 10 percent. The surfactant must of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides can be employed. The surfactant can constitute about 0.1 to about 20 percent by weight of the composition, and preferably about 0.25 to about 5 percent. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve.

A pharmaceutical composition containing a bivalent $SLe^x$ saccharide compound can be administered for prophylactic and/or therapeutic treatments. In therapeutic applications, compositions are administered to a patient already suffering from a disease, as described above, in an amount sufficient to inhibit binding between cells expressing a selectin and neutrophils or HL-60 cells; i.e., cure or at least partially arrest the symptoms of the disease and its complications. An amount adequate to accomplish this is defined as "therapeutically effective dose" or "a cellular adhesion-inhibiting amount". Amounts effective for this use depend on the severity of the disease and the weight and general state of the patient, but generally range from about 0.5 mg to about 2,000 mg of bivalent $SLe^x$ saccharide compound per day for a 70 kg patient, with dosages of from about 5 mg to about 200 mg of the compounds per day being more commonly used.

In prophylactic applications, a composition containing a contemplated compound is administered to a patient susceptible to or otherwise at risk of a particular disease. Such an amount is defined to be a "prophylactically effective dose", and again is a cellular adhesion-inhibiting amount. In this use, the precise amounts again depend on the patient's state of health and weight, but generally range from about 0.5 mg to about 2,000 mg per 70 kilogram patient, more commonly from about 5 mg to about 200 mg per 70 kg of body weight.

Single or multiple administrations of a composition can be carried out with dose levels and pattern being selected by the treating physician. In any event, the pharmaceutical formulations should provide a quantity of a bivalent SLe$^x$ saccharide compound sufficient to effectively treat the patient.

A contemplated SLe$^x$ saccharide compound can also find use as a diagnostic reagent. For example, labeled compounds can be used to locate areas of inflammation or tumor metastasis in a patient suspected of having an inflammation. For this use, the compounds can be labeled with $^{125}I$, $^{14}C$, or tritium.

BEST MODE FOR CARRYING OUT THE INVENTION

All reactions were monitored by thin layer chromatography carried out on 0.25 mm Whatman silica gel plates (60F-254) using UV light and anisaldehyde reagent [Gordon et al., "The Chemists Companion", A. Wiley-Interscience Publication, New York, p.377 (1972)] as developing agent. E. Merck silica gel (60, particle size 0.040–0.063 mm) was used for flash column chromatography.

All reactions were carried out under an argon atmosphere with anhydrous solvents from Aldrich Chemical Co., Milwaukee, Wis., unless otherwise noted. Yields refer to chromatographically and spectroscopically ($^1$H NMR) homogeneous materials unless otherwise stated. NMR spectra were recorded on a 300 MHz General Electric QE-300 NMR.

The UDP-glucose, CMP-sialic acid, uridine 5'-diphosphogalactose 4-epimerase and galactosyl transferase were purchased from Sigma Chemical Co., St. Louis, Mo. The GDP-β-fucose was purchased from Oxford Glycosystems. The N-type α(2,3)-sialyl transferase and fucosyl transferase V enzymes were prepared at Cytel Corporation, San Diego, Calif., [Ichikawa et al., *J. Am. Chem. Soc.*, 114:9283 (1992)].

EXAMPLE 1

Ethyl 4,6-O-benzylidene-2-O-benzoyl-β-D-galactospyranoside (6) and Ethyl 4,6-O-benzylidene-3-O-(trichloroacetyl-N-carbamoyl)-2-O-benzoyl-β-D-galactospyranoside (Compound 7)

Ethyl 4,6-O-benzylidene-β-D-galactopyranoside Compound 5, [Wallenfels et al., *Justis Liebigs Ann. Chem.*, 635:166 (1960)] (2.9 g, 9.8 mmol) was dissolved in CH$_2$Cl$_2$ (29 mL) and pyridine (5.4 mL) and cooled to –65° C. under argon. Chloroacetic anhydride (0.82 mL, 10.3 mmol) was then added and the reaction mixture was stirred at –65° C. for two hours. The first stage of the reaction was complete at this time, and benzoyl chloride (1.36 mL, 11.78 mmoles) was then added at –65° C. The reaction mixture was permitted to warm to room temperature, stirred overnight (about 18 hours), diluted with CH$_2$Cl$_2$ (100 mL), and washed with 1M citric acid (100 mL), water (50 mL), saturated NaHCO$_3$ (50 mL), water (50 mL), and saturated NaCl (50 mL). The organic layer was dried (Na$_2$SO$_4$), filtered and concentrated to afford a crude 2-benzoyl-3-chloroacetyl product.

The crude product was then dissolved in methanol (50 mL) and cooled to –30° C. A solution of 2M NH$_3$ in methanol (6.0 mL) was added and the reaction stirred at –30° C. for four hours to selectively cleave the chloroacetyl group. The resulting mixture was poured into CH$_2$Cl$_2$ (100 mL) and washed with water (100 mL), saturated NaHCO$_3$ (100 mL), water (100 mL), and saturated NaCl (50 mL). The organic solution was dried (Na$_2$SO$_4$), filtered, concentrated and chromatographed (silica, 80 percent ethyl acetate/hexane) to afford 1.7 g (48 percent) of Compound 6 as a white solid. $R_f$=0.3 (silica, ethyl acetate/hexane); $^1$H NMR (CDCl$_3$) δ8.07 (d, J=7.5 Hz, 2H, arom.), 7.55 (m, 3H, arom.), 7.46 (d, J=7.5 Hz, 2H, arom.), 7.38 (m, 3H, aromatic), 5.59 (s, 1H, benzylidene), 5.36 (dd, J=10.07, 8.2 Hz, 1H, H-2), 4.64 (d, J=8.2 Hz, 1H, H-1), 4.39 (dd, J=12.5, 1.1 Hz, 1H, H-6), 4.28 (d, J=4.0 Hz, 1H, H-4), 4.12 (dd, J=1.5, 12.5 Hz, 1H, H-6), 3.99–3.86 (multiple peaks, 2H, OCH$_2$CH$_3$, H-3), 3.61 (m, 1H, OCH$_2$CH$_3$), 3.56 (bs, 1H, H-5), 2.63 (d, J=9.0 Hz, 1H, OH), 1.21 (t, 3H, CH$_3$). Trichloroacetyl isocyanate was then added to the NMR sample to form Compound 7. A new low field signal was observed at 5.27 ppm (J=3.1, 9.7 Hz) typical of the H-3 of galactose. This confirmed that the H-3 position of the product was unsubstituted.

EXAMPLE 2

Ethyl 4,6-O-benzylidene-2-O-benzoyl-3-O-(3,4,6-tri-O-acetyl-2-deoxy-2-phthalimido-β-D-glucopyranosyl)-β-D-galactopyranoside (Compound 8) [Scheme 1, step b]

A suspension of molecular sieves (4 Å, 1 g), CH$_2$Cl$_2$ (10 mL), collidine (0.167 mL, 1.26 mmole), silver triflate (0.3 g, 1.16 mmole) and alcohol Compound 6 (0.71 g, 0.974 mmole) was stirred under argon for one hour. The reaction mixture was then cooled to –20° C. and a solution of 2-deoxy-2-phthalimido-3,4,6-tri-O-acetyl-β-D-glucopyranosyl bromide [Lemieux et al., *ACS Symp. Ser.*, 39:90 (1976)] (0.53 g, 1.07 mmole) in CH$_2$Cl$_2$ (1 mL) was added. The reaction mixture was stirred at –20° C. for 30 minutes, permitted to warm to room temperature and filtered through celite. The filtrate was diluted with ethyl acetate (100 mL), washed with water (50 mL), 1M citric acid (100 mL), water (50 mL), saturated NaHCO$_3$ (100 mL), water (50 mL) and saturated NaCl (50 mL) and dried (Na$_2$SO$_4$). Concentration and chromatography (silica, 40 percent ethyl acetate/toluene) afforded 0.967 g (86 percent) of Compound 8 as a white solid. $R_f$ =0.4 (silica, 70 percent ethyl acetate/hexane); $^1$H NMR (CDCl$_3$) δ7.65 (dd, J=2.9, 7.5 Hz, 2H, arom.), 7.54 (dd, J=7.6, 1.8 Hz, 2H, arom.), 7.50 (dd, J=7.0, 7.0, 2H, arom.), 7.45–7.31 (m, 6H, arom.), 7.28 (d, J=9.7 Hz, 1H, arom.), 7.25 (d, J=7.1 Hz, 1H, arom. ), 5.65 (dd, J=9.4, 10.8 Hz, 1H, H-3 Glc), 5.61 (d, J=8.6 Hz, 1H, β-anomer Glc), 5.57 (s, 1H, benzylidene), 5.38 (dd, J=8.0, 10.1 Hz, 1H, H-2 Gal), 5.16 (dd, J=9.6, 9.6 Hz, 1H, H-4 Glc), 4.52 (d, J=8.0 Hz, 1H, β-anomer Gal), 4.42–4.31 (m, 4H), 4.15 (dd, J=3.6, 12.3 Hz, 1H, H-6 Glc), 4.11 (dd, J=1.2, 12.4 Hz, 1H, H-6 Gal), 3.96 (dd, J=3.6, 10.1 Hz, 1H, H-6 Glc), 3.87–3.77 (m, 2H), 3.48–3.43 (m, 2H, OCH$_2$CH$_3$ and C-5 Gal), 2.07 (s, 3H, OAc), 2.01 (s, 3H, OAc), 1.76 (s, 3H, OAc), 0.951 (t, 3H, CH$_2$CH$_3$).

EXAMPLE 3

Ethyl 2-O-benzoyl-3-O-(3,4,6-tri-O-acetyl-2-deoxy-2-phthalimido-β-D-glucopyranosyl)-β-D-galactopyranoside (Compound 9) [Scheme 1, step c]

Benzylidene Compound 8 (1.0 g, 1.22 mmoles) was dissolved in an 80 percent solution of acetic acid in water (20 mL) and the reaction mixture heated to 80° C. for 30 minutes. The reaction mixture was then poured into a solution of saturated NaHCO$_3$ (200 mL) and solid NaHCO$_3$ was added until the pH value was neutral. The solution was extracted with ethyl acetate (100 mL) and the organic layer was washed with water (2×100 mL) and saturated NaCl(20 mL). The organic layer was dried (Na$_2$SO$_4$), concentrated and chromatographed (silica, 85 percent ethyl acetate/hexane) to afford 0.716 g (80 percent) of diol Compound 9 as a white solid. R$_f$=0.23 (silica, 80 percent ethyl acetate/ hexane); $^1$H NMR (CDCl$_3$) δ7.58 (d, J=7.9 Hz, 2H, arom.), 7.43–7.25 (bm, 5H, arom. ), 7.18 (d, J=7.7 Hz, 1H, arom. ), 7.15 (d, J=7.7 Hz, 1H, arom.), 5.66 (dd, J=10.5, 9.3 Hz, 1H, H-3 Glc), 5.59 (d, J=8.5 Hz, 1H, β-anomeric Glc), 5.29 (dd, J=9.3, 9.3 Hz, 1H, H-2 Gal), 5.11 (dd, J=9.6, 9.6 Hz, 1H, H-4 Glc), 4.46 (d, J=8.0 Hz, 1H, β-anomer Gal), 4.38–4.32 (m, 2H), 4.29–4.14 (m, 2H), 4.01–3.75 (multiple peaks, 5H), 3.61 (bt, J=5.6 Hz, 1H, H-5 Glc), 3.45 (m, 1H, OCH$_2$CH$_3$), 2.12 (s, 3H, OAc), 2.01 (s, 3H, OAc), 1.76 (s, 3H, OAc), 0.96 (t, 3H, CH$_2$CH$_3$).

EXAMPLE 4

Ethyl 3,6-Bis-O-(3,4,6-tri-O-acetyl-2-deoxy-2-phthalimido-β-D-glucopyranosyl)-2-O-benzoyl-β-D-galactopyranoside (Compound 10) and Ethyl 3,6-Bis-O-(3,4,6-tri-O-acetyl-2-deoxy-2-phthalimido-β-D-glucopyranosyl)-4-O-(trichloroacetyl-N-carbamoyl)-2-O-benzoyl-β-D-galactopyranoside (Compound 11) [Scheme 1, step d]

A suspension of molecular sieves (4 Å, 1 g), CH$_2$Cl$_2$ (10 mL), collidine (0.167 mL, 1.26 mmole), silver triflate (0.3 g, 1.16 mmole) and diol Compound 9 (0.71 g, 0.974 mmole) was stirred under argon for one hour. The reaction mixture was then cooled to −20° C. and a solution of 2-deoxy-2-phthalimido-3,4,6-tri-O-acetyl-β-D-glucopyranosyl bromide (0.53 g, 1.07 mmole) in CH$_2$Cl$_2$ (1 mL) was added. The reaction mixture was stirred at −20° C. for 30 minutes, then permitted to warm to room temperature and filtered through celite. The filtrate was diluted with ethyl acetate (100 mL), washed with water (50 mL), 1M citric acid (100 mL), water (50 mL), saturated NaHCO$_3$ (100 mL), water (50 mL) and saturated NaCl (50 mL), and dried (Na$_2$SO$_4$). Concentration and chromatography (silica, 40 percent ethyl acetate/toluene) afforded 0.967 g (86 percent) of Compound 10 as a white solid. R$_f$=0.22 (silica, 40 percent ethyl acetate/ benzene); $^1$H NMR (CDCl$_3$) δ7.95–7.76 (bd, 3H), 7.53 (dd, J=7.0, 1.1 Hz, 2H, phthalimido), 7.41 (m, 2H, benzoyl), 7.35 (m, 3H, benzoyl), 7.15 (dd, J=7.9, 7.9 Hz, 1H, phthalimido), 7.12 (dd, J=7.9, 7.9 Hz, 2H, phthalimido), 5.76 (dd, J=9.2, 10.5 Hz, 1H, H-3 Glc), 5.55 (dd, J=9.2, 10.5 Hz, 1H, H-3 Glc), 5.47 (d, J=8.5 Hz, 1H, β-anomer, Glc), 5.34 (d, J-8.5 Hz, 1H, β-anomer Glc), 5.18 (dd, J=8.8, 9.7 Hz, 2H, H-4 Glc, H-4 Glc), 5.01 (t, J=9.6 Hz, 1H, H-2 Gal), 4.38–4.06 (m, 8H), 3.94 (d, J=2.8 Hz, 1H, H-4 Gal), 3.87 (m, 2H, H-6 Gal), 3.67 (dd, J=3.1, 9.7 Hz, 1H, H-3 Gal), 3.54 (m, 1H, H-5 Glc), 3.49–3.42 (m, 1H, H-5 Gal), 3.37 (m, 1H, OCH$_2$Me), 3.14 (m, 1H, OCH$_2$Me), 2.13 (s, 3H, OAc), 2.09 (s, 3H, OAc), 2.03 (s, 3H, OAc), 2.01 (s, 3H, OAc), 1.85 (s, 3H, OAc), 1.75 (s, 3H, OAc), 0.75 (t, J=7.1 H, 3H, CH$_2$CH$_3$). Addition of trichloroacetyl-isocyanate to the NMR sample formed Compound 11 and caused a shift of the 4-position hydrogen of galactose to 5.39 (d, J=2.1 Hz, 1H) ppm.

EXAMPLE 5

Ethyl 3,6-Bis-O-(3,4,6-tri-O-acetyl-2-deoxy-2-acetamido-β-D-glucopyranosyl)-2,4-di-O-acetyl-β-D-galactopyranoside (Compound 12) [Scheme 1, step e]

A solution of trisaccharide Compound 10 (0.9 g, 0,785 mmole), hydrazine monohydrate (1.52 mL, 31.4 mmole) and ethanol (30 mL) was refluxed for eight hours. The reaction mixture was concentrated and the residue dissolved in pyridine (40 mL). Acetic anhydride (20 mL) was then added and the reaction mixture stirred for 24 hours. The reaction mixture was concentrated and the residue dissolved in CH$_2$Cl$_2$ (100 mL). The solution was washed with saturated NaHCO$_3$ (100 mL). The aqueous layer was washed again with CH$_2$Cl$_2$ (50 mL) and the combined organic layers were dried (Na$_2$SO$_4$). Concentration and chromatography (silica, 3 percent MeOH/ethyl acetate) afforded 0.57 g (76 percent) of Compound 19. as a white solid. R$_f$=0.33 (silica, 5 percent MeOH/ethyl acetate); $^1$H NMR (CDCl$_3$) δ5.43 –5.31 (m, 3H), 5.08–4.99 (m, 3H), 4.95 (d, J=8.1 Hz, 1H, β-anomer Glc), 4.77 (d, J=8.3 Hz, 1H, β-anomer Glc), 4.37 (d, J=8.0 Hz, 1H, β-anomer Gal), 4.31 (dd, J=1.2, 12.7 Hz, 1H, CH$_2$OAc), 4.24 (dd, J=4.2, 12.4 Hz, 1H, CH$_2$OAc), 4.13–4.05 (m, 2H), 3.89–3.78 (m, 4H), 3.73 –3.64 (m, 3H), 3.59–3.43 (m, 2H), 3.41 (m, 1H, OCH$_2$CH$_3$), 2.10 (s, 3H, OAc), 2.09 (s, 3H, OAc), 2.08 (s, 3H, OAc), 2.07 (s, 3H, OAc), 2.01 (s, 9H, OAc), 2.00 (s, 3H, OAc), 2.95 (s, 3H, NHAc), 1.90 (s, 3H, NHAc), 1.17 (t, J=7.0 Hz, 3H, CH$_2$CH$_3$).

EXAMPLE 6

Ethyl 3,6-Bis-O-(2-acetamido-2-deoxy-β-D-glucopyranosyl)-β-D-galactopyranoside (Compound 13) [Scheme 1, step f]

Sodium methoxide (0.1 mL, 25 percent solution in MeOH) was added to a solution of trisaccharide Compound 12 (0.366 g, 0.38 mmole) in MeOH (40 mL). The reaction mixture was stirred for 20 hours during which time a precipitate formed. Water (about 5 mL) was added until the all of the solid had dissolved and then prewashed Biogel AG 50W-X8 (hydrogen form) was added to the reaction mixture until the pH value was neutral. The reaction mixture was then filtered and the filtrate concentrated. The residue was dissolved in water (10 mL), filtered through a C-18 Sep Pack (Whatman), and the filtrate concentrated to yield 0.167 g (70 percent) of Compound 12 as a white solid. R$_f$=0.47 (silica, 30 percent 1M NH$_4$OAc/isopropanol); $^1$H NMR (D$_2$O) δ4.64 (d, J=8.4 Hz, 1H, β-anomer Glc), 4.48 (d, J=8.4 Hz, 1H, β-anomer Glc), 4.32 (d, J=7.7 Hz, 1H, β-anomer Gal), 4.06 (d, J=3.3 Hz, 1H, H-4 Gal), 3.99 (d, J=8.2 Hz, 1H), 3.91–3.83 (m, 3H), 3.74–3.61 (m, 8H), 3.59–3.38 (m, 7H), 1.99 (s, 3H, NHAc), 1.98 (s, 3H, NHAc), 1.19 (t, J=7.0 Hz, 3H, CH$_2$CH$_3$); $^{13}$C NMR (D$_2$O) δ175.0 (C=O), 174.4 (C=O), 102.7 (β-anomer), 102.4 (β-anomer), 101.4 (β-anomer), 82.1, 75.8, 75.7, 73.8, 73.6, 73.4, 69.9, 69.7, 69.6, 69.4, 68.6, 66.1, 60.7, 60.5, 55.5, 55.5, 22.2 (2C, CH$_3$C=O), 14.3 (CH$_2$CH$_3$);MS (LS1MS+) calcd. for C$_{24}$H$_{42}$N$_2$O$_{16}$Cs:747.4840, found: 747.4845.

EXAMPLE 7

Ethyl 3,6-Bis-O-[β-D-galactopyranosyl-(1→4)-2-acetamido-2-deoxy-β-D-glucopyranosyl]-β-D-galactopyranoside (Compound 14) [Scheme 2, step a]

Galactosyl transferase (EC 2.4.1.22, 6 U) and uridine 5'-diphosphogalactose 4'-epimerase (EC 5.1.3.2, 8 U) were added to a solution containing sodium cacodylate (pH 7.5, 1M, 0.4 mL), water (3.8 mL), BSA (5 percent solution, 88 μL), MnCl$_2$ (1M, 40 μL), alkaline phosphatase (EC 3.1.3.1, 1 U/μL, 44 μL), uridine diphosphoglucose disodium salt (161 mg, 0.285 mmole) and trisaccharide Compound 13 (70 mg, 0.114 mmole). The reaction mixture was inverted several times and then permitted to remain at room temperature for 72 hours. Filtration and chromatography (Biogel P-2, 0.1M NH$_4$HCO$_3$) of the filtrate afforded 100 mg (93 percent) of Compound 14 as a white solid after lyophilization. R$_f$=0.25 (silica, 30 percent 1M NH$_4$OAc/isopropanol); $^1$H NMR (D$_2$O) δ4.65 (d, J=7.8 Hz, 1H, β-anomer Glc), 4.49 (d, J=7.6 Hz, 1H, β-anomer Glc), 4.42 (d, J=7.6 Hz, 1H, β-anomer Gal), 4.41 (d, J=7.8 Hz, 1H, β-anomer Gal), 4.30 (d, J=7.8 Hz, 1H, β-anomer bridging Gal), 4.05 (d, J=3.2 Hz, 1H, H-4 Gal), 3.99–3.43 (m, 31H), 1.97 (s, 6H, OAc), 1.18 (t, 3H, CH$_2$C$\underline{H}_3$); 13C NMR (D$_2$O) δ174.9 (C=O), 174.4 (C=O), 102.9 (β-anomer), 102.8 (β-anomer), 102.6 (β-anomer), 102.3 (β-anomer), 101.3 (β-anomer), 82.2, 78.4, 78.1, 75.4 (2 C), 74.7, 74.6, 73.4, 72.5 (2 C), 72.4, 72.2, 70.1 (2 C), 69.71, 69.67, 69.4, 68.5 (2 C), 66.0, 61.0 (2 C), 60.0, 59.8, 55.3, 55.0, 22.2 (CH$_3$C=O), 17.0 (C$\underline{H}_3$C=O), 14.3 (C$\underline{H}_3$); MS (ion spray) calcd. for C$_{36}$H$_{62}$N$_2$O$_6$:938, found: 962 (M+Na$^+$), 977 (M+K$^+$).

EXAMPLE 8

Ethyl 3,6-Bis-O-[(ammonium 5-acetamido-3,5-dideoxy-α-D-glycero-D-galacto-2-nonulo-pyranosylonate acid)-(2→3)-β-D-galactopyranosyl-(1→4)-2-acetamido-2-deoxy-β-D-glucopyranosyl]-β D-galactopyranoside (Compound 14) [Scheme 2, step b]

The N-type α(2,3)-sialyl transferase (EC 2.4.99.6, 1 U) was added to a solution of cytidine-5'-monophosphate-sialic acid (0.116 g, 0.166 mmole), BSA (5 percent solution, 0.12 mL), sodium cacodylate (pH 6.5, 1M, 1.8 mL), water (5.1 mL, MnCl$_2$ (1M, 0.6 mL), alkaline phosphatase (EC 3.1.3.1, 1 U/μL, 30 μL), and pentasaccharide Compound 14 (52 mg, 55 μmole). The reaction mixture was tipped for four days. The reaction was not complete by TLC so additional cytidine-5'-monophosphate-sialic acid (0.116 g, 0.166 mmole), alkaline phosphatase (1 U/μL, 30 μL), MnCl$_2$ (1M, 0.2 mL) and N-type α(2,3)-sialyl transferase (1 U) were added and the reaction mixture tipped for another five days. Filtration and chromatography (Biogel P-2, 0.1M NH$_4$HCO$_3$) of the filtrate afforded 75 mg (86 percent) of Compound 15 as a white solid after lyophilization. R$_f$=0.15 (silica, 30 percent 1M NH$_4$OAc/isopropanol); $^1$H NMR (D$_2$O) δ4.66 (d, J=7.8 Hz, 1H, β-anomer Glc), 4.51 (bd, 3H, β-anomers of Glc, Gal, Gal), 4.32 (d, J=7.8 Hz, 1H, β-anomer, bridging Gal), 4.1–3.5 (m, 45H), 2.71 (dd, J=12.3, 4.3 Hz, 2H, H-3 (eq) sialic acid), 1.99 (s, 12H, NHAc), 1.76 (dd, J=12.5 Hz, 2H, H-3(ax) sialic acid), 1.19 (t, 3H, CH$_2$C$\underline{H}_3$); MS (ion spray) calcd. for C$_{58}$H$_{93}$N$_4$O$_{42}$:1520, found: 1519 ([M-H+]-), 759 ([M-2H$^+$]$^{2-}$).

EXAMPLE 9

Ethyl 3,6-bis-O-[(ammonium 5-acetamido-3,5-dideoxy-α-D-glycero-D-galacto-2-nonulo-pyranosylonate)-(2→3)-β-D-galactopyranosyl-(1→4)-(α-L-fucopyranosyl-(1→3))-2-acetamido-2-deoxy-β-D-glucopyranosyl]-β-D-galactopyranoside Compound 1) [Scheme 2, step c]

The fucosyl transferase V (100 mU attached to beads) was added to a solution containing sodium cacodylate (pH 6.5, 1M, 0.5 mL), water (4.5 mL), MnCl$_2$ (1M, 0.2 mL), alkaline phosphatase (32 U), GDP-fucose disodium salt (0.11 g, 0.18 mmole) and heptasaccharide Compound 15 (56 mg, 36 μmole). The reaction mixture was tipped for 48 hours. Additional enzyme (100 mU) and MnCl$_2$ (1M, 0.2 mL) was added and the reaction mixture was tipped for another four days. Filtration and chromatography (Biogel P-2, 0.1M NH$_4$HCO$_3$) of the filtrate afford 40 mg (60 percent) of Compound 1 as white solid after lyophylization. R$_f$=0.38 (silica, 40 percent 1M NH$_4$OAc/isopropanol); $^1$H NMR (D$_2$O, 500MHz) δ5.13 (d, J=3.5 Hz, 1H, α-anomer Fuc), 5.12 (d, J=3.5 Hz, 1H, α-anomer Fuc), 4.72 (d, J=8.0 Hz, 1H, β-anomer Glc), 4.59–4.51 (multiple peaks, 3H, β-anomers Glc, Gal and Gal), 4.37 (d, J=8.0 Hz, 1H, β-anomer bridging Gal), 4.10 (d, J=2.9 Hz, 1H, H-3 Gal), 4.10 (d, J=2.9 Hz, 1H, H-3 Gal), 4.03–3.47 (m, 54H), 2.77 (dd, J=12.4, 4.4 Hz, 2H, H-3(eq) sialic acids), 2.03 (s, 6H, NHAc), 2.01 (s, 6H, NHAc), 1.81 (dd, J=12.4, 1.2.4 Hz, 2H, H-3(ax) sialic acids), 1.24 (t, 3H, CH$_2$C$\underline{H}_3$), 1.18 (d, J=6.5 Hz, 6H, C$\underline{H}_3$-fucose); HRMS (LS1MS-) calcd. for C$_{70}$H$_{117}$O$_{50}$N$_2$ (M-M$^+$) 1811.6579, found: 1811.6693.

Compounds 20–23 were prepared in manners similar to those used in preparing Compound 1, the blocked galactoside corresponding to Compound 6 of Scheme 2 differing between the preparations. H-NMR data for Compounds 20–23 are provided below.

NMR DATA FOR COMPOUNDS 20–23

5-Methoxycarbonylpentyl 2,6-bis-O-[(5-acetamido-3,5-dideoxy-α-D-glycero-D-galacto-2-nonulo-pyranosylonic acid)-yl-(2→3)-β-D-galactopyranosyl-(1→4)-(α-L-fucopyranosyl-(1→3))-2-acetamido-2-deoxy-β-D-glucopyranosyl]-β-D-galactopyranoside (Compound 20) $^1$H NMR (D$_2$O, 500MHz) δ5.09 (d, J=3.5 Hz, 2H, H-1 Fuc), 4.55–4.48 (m, 3H, 3×H-1), 4.42 (d, J=7.4 Hz, 1H, H-1 Gal), 4.10–3.42 (m, 56H), 2.76 (dd, J=12.4, 4.4 Hz, 2H, H-3(eq) NeuAc), 2.42 (t, 2H, alkyl), 2.02 (s, 9H, NHAc), 2.00 (s, 3H, NHAc), 1.79 (dd, J=12.4, 12.4 Hz, 2H, H-3(ax) NeuAc), 1.63 (bm, 4H, alkyl), 1.40 (bm, 2H, alkyl), 1.15 (d, J=6.5 Hz, 6H, H-6 Fucs).

5-Methoxycarbonylpentyl 4,6-bis-O-[(5-acetamido-3,5-dideoxy-α-D-glycero-D-galacto-2-nonulo-pyranosylonic acid)-yl-(2→3)-β-D-galactopyranosyl-(1→4)-(α-L-fucopyranosyl-(1→3))-2-acetamido-2-deoxy-β-D-glucopyranosyl]-β-D-galactopyranoside (Compound 21)

$^1$H NMR (D$_2$O, 500MHz) δ5.10 (d, J=3.5 Hz, 1H, H-1 Fuc), 5.09 (d, J=3.5 Hz, 1H, H-1 Fuc), 4.73–4.62 (m, 2H, 2×H-1), 4.50 (m, 3H), 4.28 (d, J=8.0 Hz, 1H, H-1 Gal), 4.10–3.48 (m, 56H), 3.30 (dd, J=8.8 Hz, 1H, OC$\underline{H}$), 2.75 (dd, J=12.4, 4.4 Hz, 2H, H-3(eq) NeuAc), 2.40 (t, 2H, alkyl), 2.01 (s, 9H, NHAc), 1.98 (s, 3H, NHAc), 1.78 (dd, J=12.4, 12.4 Hz, 2H, H-3 (ax) NeuAc), 1.60 (bm, 4H, alkyl), 1.38 (bm, 2H, alkyl), 1.15 (d, J=6.5 Hz, 6H, H-6 Fucs).

5-Methoxycarbonylpentyl
3-O-[(5-acetamido-3,5-dideoxy-α-D-glycero-
D-galacto-2-nonulo-pyranosylonic
acid)-yl(2→3)-β-D-galactopyranosyl-(1→4)-
(α-L-fucopyranosyl-(1→3))-2-acetamido-
2-deoxy-β-D-glucopyranosyl]-4-O-[(5-acetamido-
3,5-dideoxy-α-D-glycero-D-galacto-
2-nonulo-pyranosylonic
acid)-yl-(2→3)-β-D-galactopyranosyl-
(1→4)-2-acetamido-2-deoxy-β-D
-glucopyranosyl]-β-D-galactopyranoside and
5-Methoxycarbonylpentyl
4-O-[(5-acetamido-3,5-dideoxy-α-D-glycero-
D-galacto-2-nonulo-pyranosylonic
acid)-yl-(2→3)-β-D-galactopyranosyl-(1→4)-
(α-L-fucopyranosyl-(1→3))
-2-acetamido-2-deoxy-β-D-glucopyranosyl]-
3-O-[(5-acetamido-3,5-dideoxy-α-D-glycero-
D-galacto-2-nonulo-pyranosylonic
acid)-yl-(2→3)-β-D-galactopyranosyl-(1→4)-
2-acetamido-2-deoxy-β-D-glucopyranosyl]-β-
D-galactopyranoside (Compound 22)

$^1$H NMR (D$_2$O, 500MHz) δ5.15 (d, H-1 Fuc), 5.08 (d, H-1 Fuc), 5.12 (d, J=3.5 Hz, 1H, H-1 Fuc), 4.67–4.45 (m, H-1), 4.30 (d, H-1), 4.12–3.45 (m), 2.75 (dd, J=12.4, 4.4 Hz, H-3(eq) NeuAc), 2.39 (t, alkyl), 2.02 (s, 12H), 1.77 (dd, J=12.4, 12.4 Hz, H-3(ax) NeuAc), 1.62 (m, alkyl), 1.36 (alkyl), 1.14 (d, H-6 Fucs).

5-Methoxycarbonylpentyl
3-O-[(5-acetamido-3,5-dideoxy-α-D-glycero-
D-galacto-2-nonulo-pyranosylonic
acid)-yl-(2→3)-β-D-galactopyranosyl-(1→4)-
(α-L-fucopyranosyl-(1→3))-2-acetamido-2-
deoxy-β-D-glucopyranosyl]-2-O-[(5-acetamido-
3,5-dideoxy-α-D-glycero-D-galacto-2-nonulo-
pyranosylonic
acid)-yl-(2→3)-β-D-galactopyranosyl-(1→4)-
2-acetamido-2-deoxy-β-D-glucopyranosyl]-β-
D-galactopyranosylonic and
5-Methoxycarbonylpentyl
2-O-[(5-acetamido-3,5-dideoxy-α-D-glycero-
D-galacto-2-nonulo-pyranosylonic
acid)-yl-(2→3)-β-D-galactopyranosyl-(1→4)-
(α-L-fucopyranosyl-(1→3))-2-acetamido-
2-deoxy-β-D-glucopyranosyl]-3-O-[(5-
acetamido-3,5-dideoxy-α-D-glycero-D-
galacto-2-nonulo-pyranosylonic
acid)-yl-(2→3)-β-D-galactopyranosyl-(1→4)-
2-acetamido-2-deoxy-β-D-glucopyranosyl]-β-
D-galactopyranoside (Compound 23)

$^1$H NMR (D$_2$O, 500MHz) δ5.085 (d, H-1 Fuc), 5.08 (d, H-1 Fuc), 5.12 (d, J=3.5 Hz, 1H, H-1 Fuc), 4.67–4.45 (m, H-1's), 4.12–3.45 (m), 2.75 (dd, J=12.4, 4.4 Hz, H-3(eq) NeuAc), 2.39 (t, alkyl), 2.07, 2.04, 2.00 (s, 12 H), 1.77 (dd, J=12.4, 12.4 Hz, H-3 (ax) NeuAc), 1.62 (m, alkyl), 1.36 (alkyl), 1.14 (d, H-6 fucs).

Cellular Binding Assays

A modified recombinant soluble E-selectin/HL-60 cell adhesion assay was developed to provide a simple and highly reproducible method with which to compare the E-selectin blocking potential of a bivalent SLe$^x$ saccharide compound. In this assay, recombinant soluble E-selectin (rELAM) is bound to the plastic surface of a 96 well ELISA plate. Dilutions of bivalent SLe$^x$ saccharide compounds to be assayed are added to the wells followed by HL-60 cells which bear the ligand for E-selectin. The cells are allowed to adhere to the E-selectin coated assay plate and the nonadherent cells are removed by washing the plate with an automated plate washer. Bound cells are quantitated by measuring the cellular enzyme myeloperoxidase. The molar concentration of assayed bivalent SLe$^x$ saccharide required to achieve 50 percent inhibition of control adhesion such as that inhibited by free SLe$^x$ or an analog is used to compare the contemplated analogs for potency. The efficacy of using a similar bound recombinant soluble portion of ELAM-1 as a substrate for binding HL-60 and other cells that bind to cells containing the ELAM-1 (E-selectin) receptor has been demonstrated by Lobb et al., *J. Immunol*, 147:124–129 (1991).

MATERIALS AND METHODS

Materials

ELISA plate, Immulon 2 (Dynatec Laboratories) (Fisher 14-245-61)

0.2m filter units (Nalgene #150–0020)

rELAM (recombinant modified ELAM-1) affinity purified, prepared as follows below. Each batch of rELAM was tested functionally to determine the appropriate concentration for use in the assay. A batch was titrated over a range of 1–5 μg/mL using inhibition by Compound Z (described hereinafter) as the standard. Small aliquots were then prepared, quick frozen in a dry-ice acetone bath and stored at −70° C. Each aliquot was opened only one time and then discarded or saved for use in other types of assays.

The soluble form of E-selectin (rELAM or sol-E-selectin) used here was engineered by deleting the transmembrane domain from the cDNA. This recombinant cDNA was cloned into a mammalian expression vector pCDNA1 [a derivative of pCDM8; Seed, *Nature*, 329:840 (1987)] that contains the chimeric cytomegalovirus/human immunodeficiency virus promoter. When introduced into the adenovirus-transformed human kidney cell line 293, expression of the CMV promoter is efficiently activated by the E1 gene products by a mechanism that has not been fully delineated. The pCDNA1-sol-E-selectin construction was introduced, via calcium phosphate-mediated gene transfer, into 293 cells and a stable cell line expressing high levels of sol-E-selectin was generated. The sol-E-selectin produced by these cells was purified by immunoaffinity chromatograph on an anti-E-selectin monoclonal antibody Protein-A Sepharose column.

More specifically, the adenovirus transformed human kidney cell line 293 was obtained from the ATCC (CRL-1573). 293 Cells were grown as adherent cultures in DMEM, obtained from Whittaker Bioproducts (Walkersville, Md.), supplemented with 10 percent fetal bovine serum (FBS), obtained from JRH Biochemical (Lenexa, Kans.).

The plasmid pCDNA1, a derivative of pCDM8 [Seed, *Nature*, 339:840 (1987)], was obtained from Invitrogen (San Diego, Calif.). The plasmid pBluescript II was obtained from Stratagene (San Diego, Calif.). The plasmid pSV2-neo [Southern et al., *J. Mol. Appl. Gen.*, 1:327 (1982)] contains the *E. coli* gene encoding the aminoglycoside 3'-phosphotransferase gene. When pSV2-neo is introduced into mammalian cells, the transfected cells exhibit resistance to the antibiotic G418.

A 1.67 Kbp DNA fragment encoding a truncated structural gene for E-selectin was isolated by polymerase chain reaction (PCR) amplification of cDNA derived from messenger RNA that was isolated from IL-1-activated human endothelial cells. The 5'-amplimer inserted a unique ClaI restriction site 28 nucleotides upstream from the initiation codon of the E-selectin structural gene. The 3'-amplimer inserted the termination codon TGA after amino acid number 527 of the mature E-selectin, followed by a unique XhoI restriction site. The carboxy-terminus of sol-E-selectin is located at the carboxy terminus of the sixth consensus repeat element, thereby deleting the transmembrane domain. The 1.67 Kbp PCR fragment was codigested with ClaI and XhoI restriction endonucleases and sub-cloned into the ClaI and XhoI restriction sites of the cloning vector pBluescript II, providing vector pBS11-sol-E-selectin. Expressed soluble-E-selectin is 527 amino acid residues in length and contains 11 potential N-glycosylation sites.

A 1.67 Kbp DNA fragment containing the sol-E-selectin cDNA was isolated from pBS11-sol-E-selectin and sub-cloned into the EcoRV and XhoI sites of the expression vector pCDNAI, thereby providing vector pCDNAI-sol-E-selectin.

pCDNAI-sol-E-selectin was cotransfected with pSV2-neo, via the calcium phosphate technique [Kriegler, *Gene Transfer and Expression: A Laboratory Manual*, W. H. Freeman, New York, N.Y. (1991)] into 293 cells. Forty-eight hours post-transfection, the transfected 293 cells were trypsinized and plated into DMEM, 10 percent FBS, and 600 μg/mL (potency) of G418 (Geneticin, Sigma). The selection medium was changed every three days until a stable G418-resistant population was established.

Single clones of G418-resistant cells were isolated by cloning cylinders. Isolated clones were screened for the synthesis of sol-E-selectin by enzyme-linked immunosorbent assay (ELISA) utilizing the anti-E-selectin monoclonal antibody designated CY1787 as the primary antibody. Positive clones were plated at $10^6$ cells/100 mm dish. They were metabolically labeled 24 hours later with [$^{35}$S]-methionine for five hours. Labeled sol-E-selectin was immunoprecipitated from the medium with the anti-E-selectin monoclonal antibody CY1787 and electrophoresed through a 10 percent PAGE gel, the gel dried and subjected to autoradiograph. Clone 293#3 was selected as the stable cell line that produced the greatest amount of the 110-Kd sol-E-selectin protein/cell.

A 10-chambered Nuc Cell Factory (6250 cm$^2$ total surface area, Nunc) was seeded with $2.78 \times 10^8$ cells (clone 293#3) in 850 mL in DMEM supplemented with five percent FBS and incubated at 37° C. for 72 hours. The medium was harvested and replaced with 850 mL of DMEM five percent FBS. After the cell factory was incubated at 37° C. for 48 hours, the medium was harvested a second time and replaced with 850 mL DMEM, five percent FBS. After the cell factory was incubated at 37° C. for 48 hours, the medium was harvested a third (and final) time.

After each harvest, 0.02 percent sodium azide was added to the medium. The medium was clarified by centrifugation (5000 ×g), passed through a 0.2 μm filter and stored at 4° C. until further purification.

Monoclonal antibody CY1787 was conjugated to protein-A Sepharose essentially as described by Schneider et al., *J. Biol. Chem.*, 257:10766 (1982). Briefly, 28 mg of monoclonal CY1787 (5 mg/mL) in PBS was mixed with 5 mL of protein-A Sepharose for 30 minutes at room temperature. The beads were then washed four times by centrifugation with 25 mL of 0.2M borate buffer, pH 8.2, followed by two washes with 10 mL of 0.2M triethanolamine, pH 8.2. The resin was then suspended in 40 mL of 0.2M triethanolamine buffer, pH 8.2, containing 0.02M dimethylpimelimidate. After reacting for 45 minutes at room temperature on a rotator, the resin was washed twice with 0.02M ethanolamine, pH 8.2, followed with three washes with 10 mL of 0.2M borate buffer, pH 8.2. Unbound antibody was removed by elution with 0.1M sodium acetate buffer, pH 4.5. Of the antibody applied, 89 percent was conjugated to the protein-A Sepharose.

Tissue culture supernatant (2550 mL) was passed through a 0.7 cm×1.5 cm pre-column of protein-A Sepharose connected in series to a 1.5 cm×3 cm affinity column of CY1787-protein-A Sepharose at a flow rate of 20 mL/hr. The columns were then disconnected and the CY1787-containing affinity column was washed with 20 mM Tris buffer, pH 7.5, containing 150 mM NaCl and 2 mM CaCl$_2$ until the absorbance at 280 nm of the eluate approached zero. Bound E-selectin was eluted with 0.1M sodium acetate buffer, pH 3.5, containing 1 mM CaCl$_2$ using gravity flow. Fractions (1 mL) were collected into 300 μL of 2M Tris, pH 10. Protein-containing fractions were pooled and dialyzed against DPBS. Following concentration of an Amicon Centriprep 30 until the protein concentration was approximately 1 mg/mL, the purified E-selectin was aliquoted and stored at −80° C. Purity was greater than 90 percent by SDS-PAGE. A total of 10 mg of E-selectin was purified from 2550 mL of cell culture medium.

Dulbecco's PBS (Dulbecco's phosphate buffered saline; DPBS) (Whittaker, 17–513B)

HL-60 (ATCC, CCL 240) A large batch of HL-60 cells was grown up, tested for function in the assay and verified mycoplasma free. The cells were frozen at −180° C. in 10 percent DMSO, 10 percent Fetal Calf Serum, 80 percent RPMI 1640 (Whittaker) at $15 \times 10^6$ cells per vial in 2 mL cryovials. Freezing was performed using a controlled rate freezer.

Compound Z standard SLe$^x$ pentasaccharide-OEt:

NeuAcα2→3Galβ1→4[Fucα1→3]GlcNAcβ1→3GalβOEt

The Compound Z Standard was prepared as a 10 mM solution in DPBS. The solution was stored at −20° C.

| Neutrophil wash buffer (NWB): | |
|---|---|
| 10× HBSS (Hank's balanced salt solution; Gibco, 310-4065) | 20 mL |
| 1M HEPES (Gibco, 380-5630) | 2 mL |
| Super Q H$_2$O | 178 mL |
| D-Glucose (Sigma, G 7021) | 0.4 g |
| | 200 mL |

Made fresh daily or stored sterilized solution at 4° C. pH to 7.2–7.4, filter sterilized (0.2 μ).

| 100 mM CaCl$_2$ stock: | |
|---|---|
| Calcium chloride, anhydrous (Baker, 1308) | 1.11 g |
| Super Q H$_2$O | 100 mL |
| Filter sterilized (0.2 m) | 100 mL |

Neutrophil wash buffer+1mM CaCl$_2$+0.1 percent BSA (NWB/Ca/BSA):

| | |
|---|---|
| Bovine serum albumin (Sigma, A-6918) | 10 g |
| 100 mM CaCl₂ stock | 100 mL |
| NWB to | 1000 mL | pH to 7.2 to 7.4. Filter sterilized (0.2μ), store stock at 4° C.

| Blocking Buffer: | |
|---|---|
| DPBS (Whittaker, 17-513B | 100 mL |
| Bovine Serum Albumin (Sigma, A-6918) | 1 g |
| | 100 mL | pH to 7.2 to 7.4. Filter sterilized (0.2μ), stock stored at 4° C.

| Citric Acid Soln, 0.1M: | |
|---|---|
| Citric acid, anhydrous, free acid (Sigma, C-0759) | 10.5 g |
| Super Q H₂O | bring to 500 mL |

Prepare in volumetric or graduated cylinder. Stored at room temperature.

| Sodium Phosphate Soln, 0.2M: | |
|---|---|
| Sodium phosphate, dibasic, anhydrous (Na₂HPO₄) (Sigma, S-0876) | 14.2 g |
| Super Q H₂O | bring to 500 mL |

Prepared in volumetric or graduated cylinder. Stored at room temperature.

| Citrate/Phosphate buffer: | |
|---|---|
| Citric acid soln (0.1M) | 24.3 mL |
| Sodium phosphate soln (0.2M) | 25.7 mL |
| Super Q H₂O | 50 mL |
| | 100 mL |

Stored at room temperature.

| Cell Lysis Buffer: | |
|---|---|
| Nonidet P 40 (NP-40) (Sigma, N-6507 | 0.1 g |
| 0.1M Citrate | 24.3 mL |
| 0.2M Sodium phosphate, dibasic | 25.7 mL |
| Super Q H₂O | 50 mL |
| | 100.0 mL |

Stored at room temperature.

| OPDA (o-phenylenediamine): | |
|---|---|
| Citrate-phosphate buffer | 10 mL |
| o-Phenylenediamine dihydrochloride (Sigma, P 8287) | 10 mg |
| H₂O₂ (Sigma, H 1009) | 10 μL |
| | 10 mL |

Made immediately before use. Hydrogen peroxide was stored in the dark at 10° C.

| H₂SO₄ Stop buffer, 4N | |
|---|---|
| Sulfuric acid, 18M (Fisher, A300s-212) | 111 mL |
| Super Q H₂O | to 500 mL |

Method

1. Assays were carried out in 96-well Immunolan 2 plates (Dynatech Laboratories, Inc., Chantilly, Va. catalog #011-0103655). The rELAM (sol-E-selectin) was diluted to the appropriate concentration for the current batch. For these assays, rELAM was used at 2.5 or 3.0 μg/mL in DPBS; with well coating being carried out at room temperature. Using a multichannel pipette, 50μl per well were added to the following wells of one ELISA plate: E1-E6, F1-F6, and G1-G6. DPBS (50μl) was added to wells H1, H2, and H3 for use as controls. This plate is referred to as the pretest plate.

One additional assay plate was coated for every three unknown samples to be assayed. Again, using a multichannel pipette, 50 μL of the diluted rELAM was added to the following wells of the plates: B1-B12, C1–C12, D1-D12, E1-E12, F1-F12, G1-G12. DPBS (50 μl) to wells H1, H2, and H3 for use as controls. These plates are known as the sample plates. These plates were covered with foil and incubated three hours at room temperature.

2. The plates were washed three times with 200 μL blocking buffer. The wells were refilled with 200 μL blocking buffer, covered with foil and incubated at room temperature for one hour.

3. Three vials of frozen HL-60 cells were thawed for every two sample plates prepared. The vials were quick-thawed in a 37° C. water bath. The cells were pipetted into a 15 mL centrifuge tube containing 10 mL of ice cold NWB 1 percent BSA. The cells were centrifuged for seven minutes at 1200 rpm in a 4° C. centrifuge, and washed two more times in NWB/BSA. The cells were counted using a hemocytometer and resuspended to 107/mL in NWB+1 percent BSA+1mM CaCl₂.

4. While the cells were being washed, the standard and assay compound solutions were prepared. The bivalent SLe$^x$ saccharide compounds to be assayed were weighed into 1.5 mL eppendorf tubes and enough DPBS was added to make each sample a 10 mM solution according to its molecular weight. A 6 μL aliquot of each sample was removed and 2 μL were dotted on each square of a of a pH test strip. If the sample was not pH 7–7.4, the pH value was adjusted to that range or the compound was not assayed. The assay requires 180 μL of a 10 mM solution of each compound solution to be used and 180 μL of a 10 mM solution of the Compound Z Standard for each plate to be run including the test plate. Serial dilutions of inhibitors were prepared from the 10 mM solutions by dilution in NWB.

5. The blocked ELISA plates were inverted and flicked, and blotted by tapping vigorously on paper towels to remove all liquid from the wells. To each well were then added 40 μL of NWB+1 percent BSA+1 mM Ca$^{+2}$ using a multichannel pipette.

6. All of the liquid was removed from wells E6 and G6 of the pretest plate. An aliquot of 40 μL of 10 mM stock of Compound Z was added to each of the empty wells, as well as to wells E5 and G5. The solution in well E5 was mixed by pipetting up and down 10 times with a p 200 pipetteman set at 40 μL. A 40 μl aliquot of solution was removed from the well and diluted serially across the plate in well E4 then E3 and then E2, each time mixing 10 times. A 40 μl aliquot was removed and discarded from the last well. This procedure was repeated for rows G4 to G2.

7. HL-60 cells ($2 \times 10^5$) were added to each well (except H1) in 20 μl using a multichannel pipette. The plate was placed on a plate shaker for five seconds, and let stand 15 minutes at room temperature.

8. The plate was washed using a Molecular Devices Microplate washer (Model #4845-20) adjusted for slow liquid delivery and set on 3 washes per well, with NWB+1 percent BSA+1 mM $CaCl_2$ as the wash solution.

9. Cell Lysis Buffer (50 μL per well) was added and the plate placed on plate shaker for five minutes at room temperature.

10. A 50 μL aliquot per well of OPDA solution was added, and the plate was placed on the plate shaker for ten minutes at room temperature to assay for the production of myeloperoxidase released from the HL-60 cells.

11. The color-forming reaction was stopped after ten minutes by the addition of 40 μL per well of $H_2SO_4$ Stop buffer, and the optical density (O.D.) for the wells of the plate was read at 492 nm in a TiterTex plate reader, subtracting well $H_1$ as the blank.

12. The negative control was determined by taking the mean of the O.D. values for wells H2 and H3. This is the "no-E-selectin negative binding control". The "positive binding control" was calculated for the standard curve as the mean of wells E1, F1, F2, F3, F4, F5, F6, and G1. If the "no-E-selectin negative binding control" was greater than 10 percent of the mean "positive binding control", the assay was not continued. If that value was less than or equal to 10 percent of the mean "positive binding control", sample duplicates (E6, G6), (E5, G5), (E4, G4), (E3, G3) and (E2, G2) were averaged. Each duplicate average was divided by the mean "positive binding control" value to give percentage of positive binding for each concentration of assayed compound. The "positive binding control" percent was plotted vs log concentration of inhibitor. The 50 percent inhibition point was determined from the graph. This point should lie between 0.5 and 1.5 mM, and if not, the assay did not continue.

13. If the pretest plate standard curve was within the acceptable limits, the remainder of the assay proceeded. The standard Compound Z was diluted on each sample plate as in step 6. Assayed compounds were diluted similarly. Assayed bivalent $SLe^x$ saccharide compounds were placed on the plate according to the following template:

| Conc. | | Assay #1 | Assay #2 | Assay #3 |
| --- | --- | --- | --- | --- |
| 6.6 mM | or Dil. 1 | B6, D6 | B7, D7 | E7, G7 |
| 3.3 mM | Dil. 2 | B5, D5 | B8, D8 | E8, G8 |
| 1.65 mM | Dil. 3 | B4, D4 | B9, D9 | E9, G9 |
| 0.82 mM | Dil. 4 | B3, D3 | B10, D10 | E10, G10 |
| 0.412 mM | Dil. 5 | B2, D2 | B11, D11 | E11, G11 |

14. When all assay samples were diluted on the plate, HL-60 cells were added as in step 7 above and the procedure followed through step 11 as above.

15. The mean "positive binding control" was calculated for assay #1 from wells B2, C1–6 and D2; for assay #2 from wells B12, C7–12 and D12; and for assay #3 from wells E12, F7–12 and G12. The percent of positive binding for each dilution of each assay was graphed and the 50 percent inhibition point determined from the graph. Activity for each bivalent $SLe^x$ saccharide compound was recorded as a ratio of the 50 percent binding value for the standard Compound Z divided by the 50 percent binding value for the assayed bivalent $SLe^x$ saccharide sample. The value for $SLe^x$ itself was similarly determined.

Values for $SLe^x$ itself and ratios to Compound Z for several contemplated bivalent $SLe^x$ saccharide compounds are provided in Table 1, below. Ratios of those $IC_{50}$ values corrected to be relative to $SLe^x$ are determined by dividing the value shown by 0.76.

TABLE 1

E-Selectin Cell Adhesion Assay

| Compound | Compound No. | Ratio $\left( \dfrac{\text{Compound Z IC}_{50}}{\text{Compound IC}_{50}} \right)$ |
| --- | --- | --- |
| [structure] | $SLe^x$ | 0.76 |

TABLE 1-continued

E-Selectin Cell Adhesion Assay

| Compound | Compound No. | Ratio $\left(\dfrac{\text{Compound Z IC}_{50}}{\text{Compound IC}_{50}}\right)$ |
|---|---|---|
| [structure] | 1 | 3.8 |
| | | 2.67 |
| [structure] | 20 | 2.67 |

TABLE 1-continued
E-Selectin Cell Adhesion Assay
| Compound | Compound No. | Ratio $\left(\dfrac{\text{Compound Z IC}_{50}}{\text{Compound IC}_{50}}\right)$ |
|---|---|---|
| 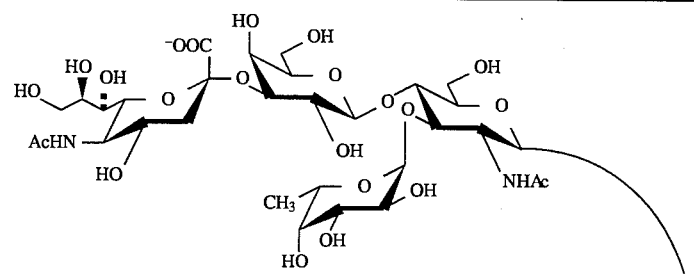 | 21 | 1.67 |
| 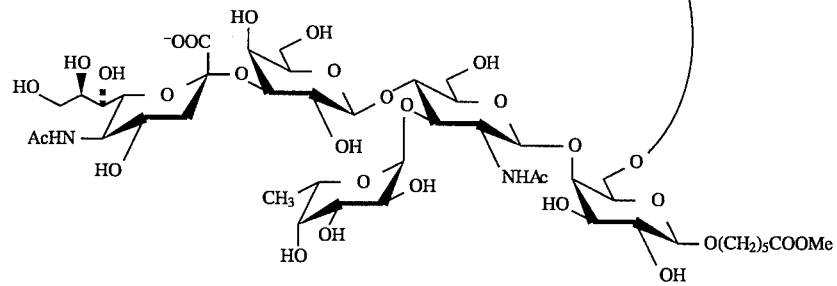 | 22 | 1.75 |
| 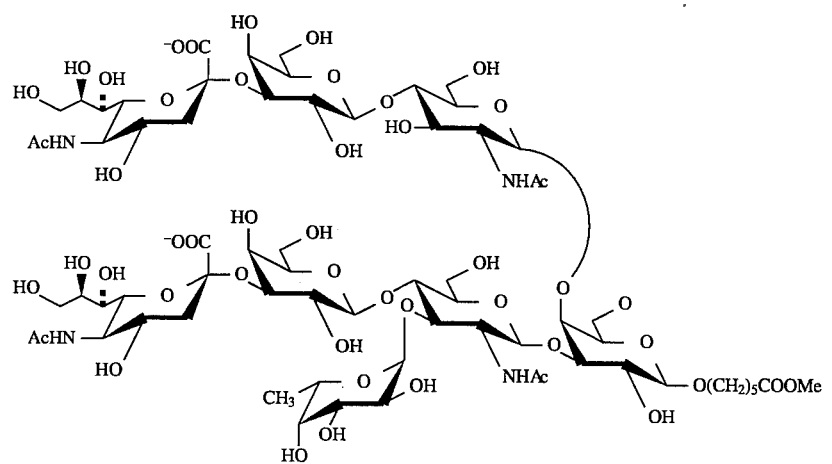 | 23 | 1.75 |

Examination of the above data shows that the $IC_{50}$ value ratio of $SLe^x$ to that of each of the exemplary bivalent $SLe^x$ saccharides was greater than two. That ratio for Compound 1 was about 3.5–5, whereas that ratio for Compound 20 was about 3.5.

FIG. 1 shows the results of binding inhibition studies carried out over a range of concentrations using Compounds 1, 20, 21, 22 and 23 as well as Compound Z. As is seen from that figures, Compound 1 was the most active, followed by Compounds 23 and 22 that were more active than Compound 21, that itself was more active than Compound 20. All five of the dimers (bivalent $SLe^x$ saccharide compounds) were quite a bit more active than the pentasaccharide Compound Z. In vivo studies using $SLe^x$ for protection against lung injury in rats indicate that the in vivo $IC_{50}$ value is about 1 μM. Mulligan et al., Nature., 364:149 (1993).

Detailed conformational analysis of Compound 1, as well as Compounds 20 and 21, using $^1H$ NMR carried out by Dr. Chi-Huey Wong and co-workers of the Department of Chemistry, The Scripps Research Institute, La Jolla, Calif. indicate that the $SLe^x$ domains of each of the dimers exists in basically the same configuration as monomeric $SLe^x$. Differences in the activity of the dimers most likely derive from differences in the relative orientation and distance between $SLe^x$ domains.

The foregoing description and the examples are intended as illustrative and are not to be taken as limiting. Still other variations within the spirit and scope of this invention are possible and will readily present themselves to those skilled in the art.

We claim:

1. A compound having the structure

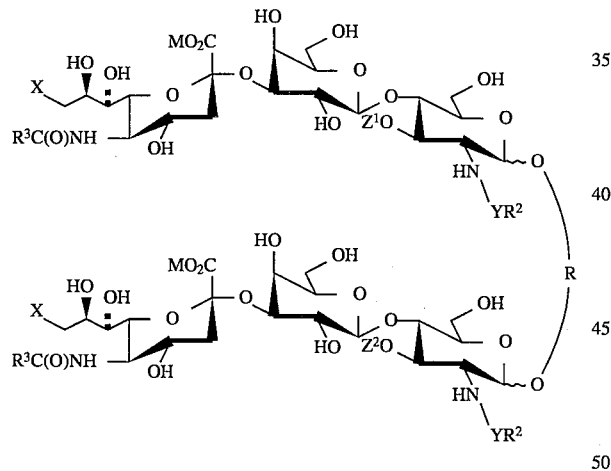

wherein R is a directly linked divalent monosaccharide unit;

Y is selected from the group consisting of C(O), $SO_2$, HNC(O), OC(O) and SC(O);

$R^2$ is selected from the group consisting of a $C_1$–$C_{18}$ aliphatic, an aryl, a substituted aryl and a phenyl $C_1$–$C_3$ alkylene group, wherein said aryl group has one six-membered aromatic ring or two fused six-membered aromatic rings, which ring or rings are hydrocarbyl, monoazahydrocarbyl, or diazahydrocarbyl rings, and said substituted aryl group is a before-mentioned aryl group having a substituent selected from the group consisting of halo, trifluoromethyl, nitro, $C_1$–$C_6$ alkyl, $C_1$–$C_6$ alkoxy, amino, mono-$C_1$–$C_6$ alkylamino, di-$C_1$–$C_6$ alkylamino, benzylamino and $C_1$–$C_6$ alkylbenzylamino;

$R^3$ is methyl or hydroxymethyl;

X is selected from the group consisting of hydroxyl, $C_1$–$C_6$ acyloxy, $C_2$–$C_6$ hydroxylacyloxy, halo and azido;

$Z^1$ and $Z^2$ are α-L-fucosyl or hydrogen (H), but at least one of $Z^1$ and $Z^2$ is α-L-fucosyl; and M is a proton ($H^+$) or a pharmaceutically acceptable cation.

2. The compound according to claim 1 wherein $Z^2$ is hydrogen.

3. The compound according to claim 1 wherein $Z^1$ is hydrogen.

4. The compound according to claim 1 wherein both $Z^1$ and $Z^2$ are α-L-fucosyl.

5. The compound according to claim 1 wherein R has a structure selected from the group consisting of

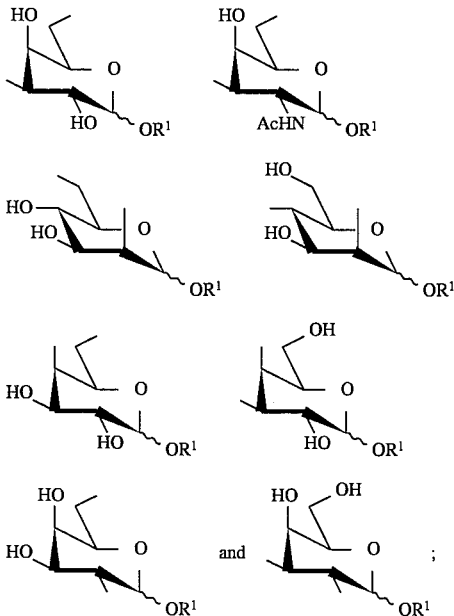

wherein $R^1$ is selected from the group consisting of hydrogen, a $C_1$–$C_{18}$ straight chain, branched chain or cyclic hydrocarbyl, a $C_1$–$C_6$ alkyl $C_1$–$C_5$ alkylene ω-carboxylate, and an ω-tri($C_1$–$C_4$ alkyl/phenyl)silyl $C_2$–$C_4$ alkylene group, or $OR^1$ together form a $C_1$–$C_{18}$ straight chain, branched chain or cyclic hydrocarbyl carbamate.

6. A compound of the formula

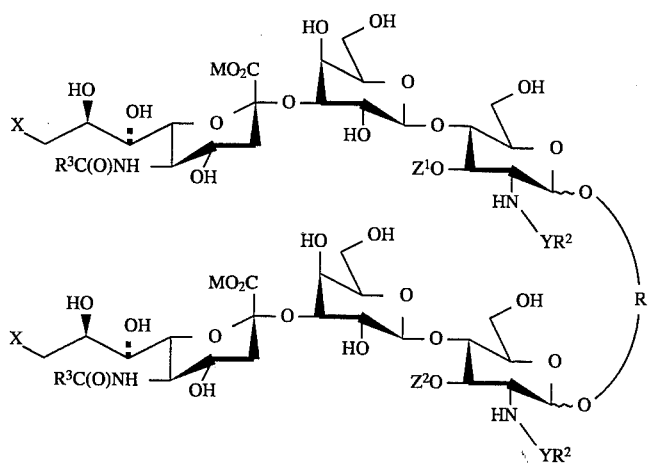

wherein R is selected from the group consisting of

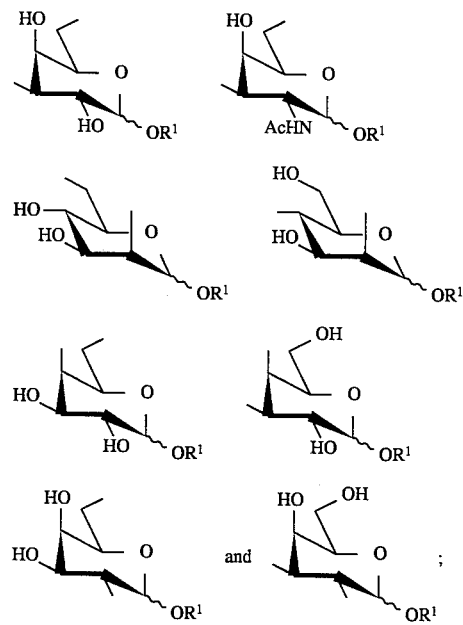

$R^1$ is selected from the group consisting of hydrogen, a $C_1-C_{18}$ straight chain, branched chain or cyclic hydrocarbyl, a $C_1-C_6$ alkyl $C_1-C_5$ alkylene ω-carboxylate and an ω-tri($C_1-C_4$ alkyl/phenyl)silyl $C_2-C_4$ alkylene group, or $OR^1$ together form a $C_1-C_{18}$ straight chain, branched chain or cyclic hydrocarbyl carbamate;

Y is selected from the group consisting of C(O), $SO_2$, HNC(O), OC(O) and SC(O);

$R^2$ is selected from the group consisting of a $C_1-C_{18}$ aliphatic, an aryl, a substituted aryl and a phenyl $C_1-C_3$ alkylene group, wherein said aryl group has one six-membered aromatic ring or two fused six-membered aromatic rings, which ring or rings are hydrocarbyl, monoazahydrocarbyl, or diazahydrocarbyl rings, and said substituted aryl group is a before-mentioned aryl group having a substituent selected from the group consisting of halo, trifluoromethyl, nitro, $C_1-C_6$ alkyl, $C_1-C_6$ alkoxy, amino, mono-$C_1-C_6$ alkylamino, di-$C_1-C_6$ alkylamino, benzylamino and $C_1-C_6$ alkylbenzylamino;

$R^3$ is methyl or hydroxymethyl;

X is selected from the group consisting of hydroxyl, $C_1-C_6$ acyloxy, $C_2-C_6$ hydroxylacyloxy, halo and azido;

$Z^1$ and $Z^2$ are α-L-fucosyl or hydrogen (H), but at least one of $Z^1$ and $Z^2$ is α-L-fucosyl; and M is a proton ($H^+$) or a pharmaceutically acceptable cation.

7. The compound according to claim 6 wherein Y is carbonyl.

8. The compound according to claim 7 that has a structure corresponding to the formula

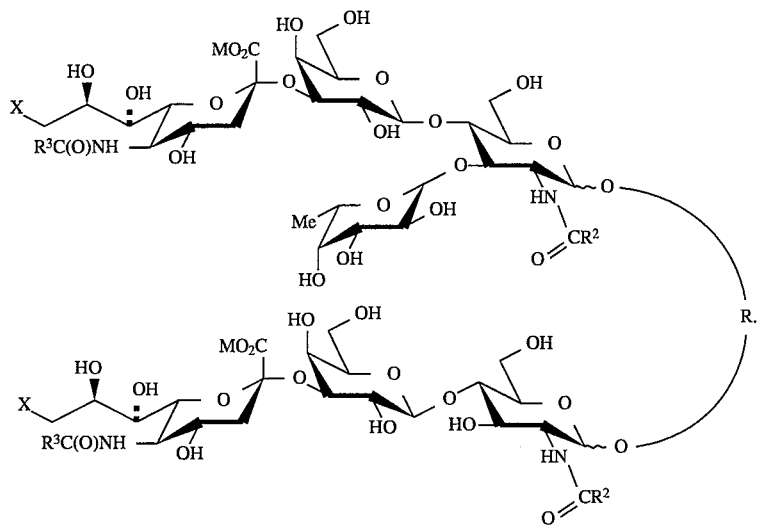
9. The compound according to claim 8 wherein R is a divalent galactoside.
10. The compound according to claim 9 that corresponds to the formula
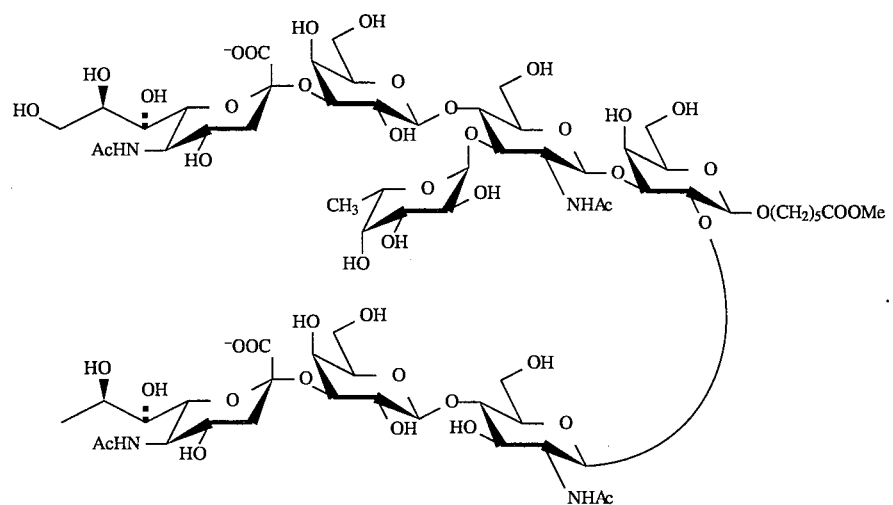
11. The compound according to claim 7 that has a structure corresponding to the formula

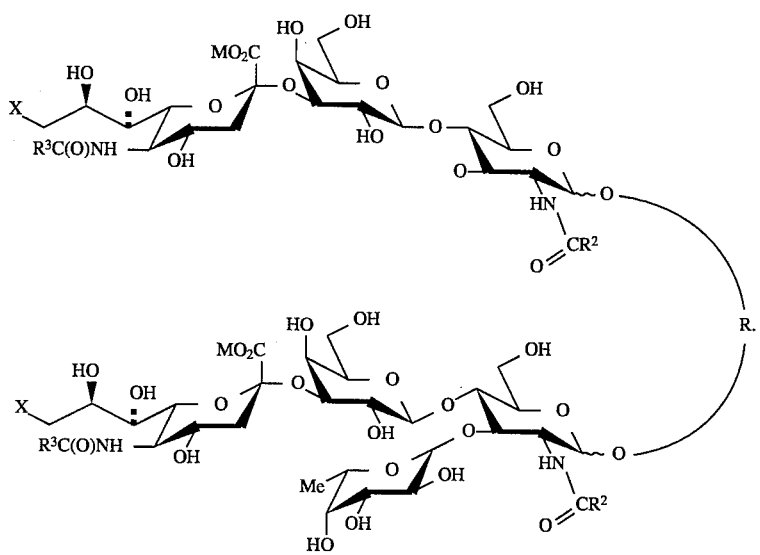
12. The compound according to claim 11 wherein R is a divalent galactoside.
13. The compound according to claim 12 that corresponds to the formula
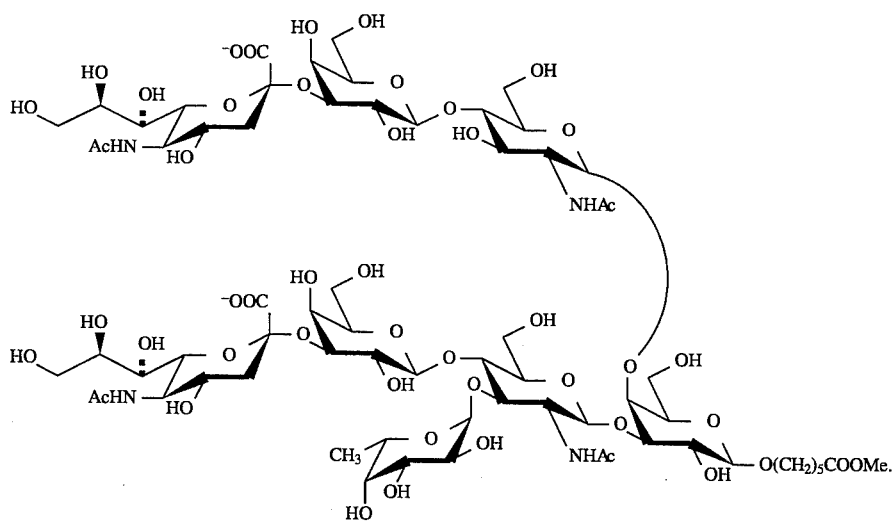
14. The compound according to claim 7 that has a structure corresponding to the formula

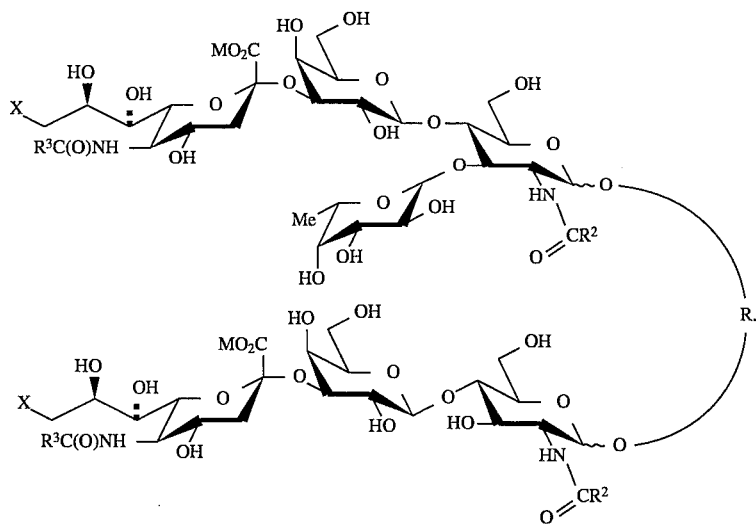
15. The compound according to claim 14 wherein R is a divalent galactoside.
16. The compound according to claim 15 that corresponds to the formula
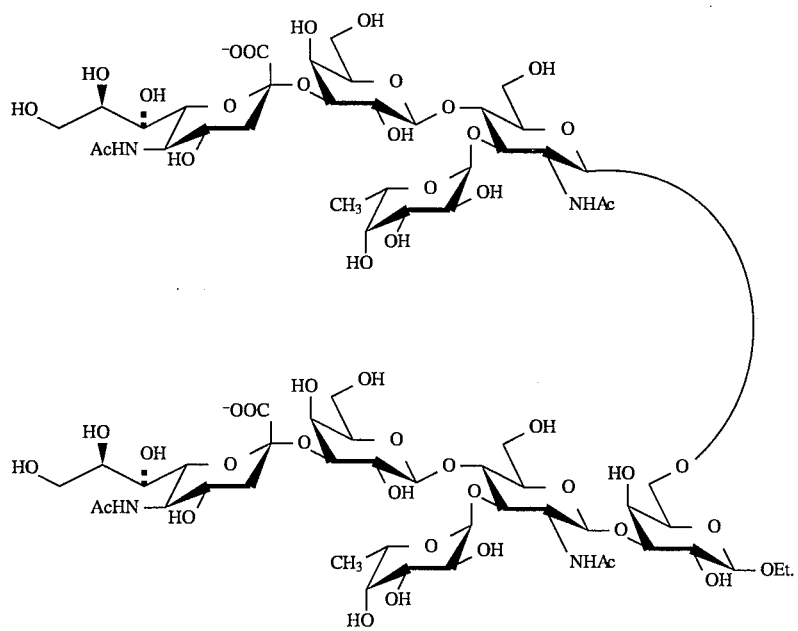
17. The compound according to claim 15 that corresponds to the formula

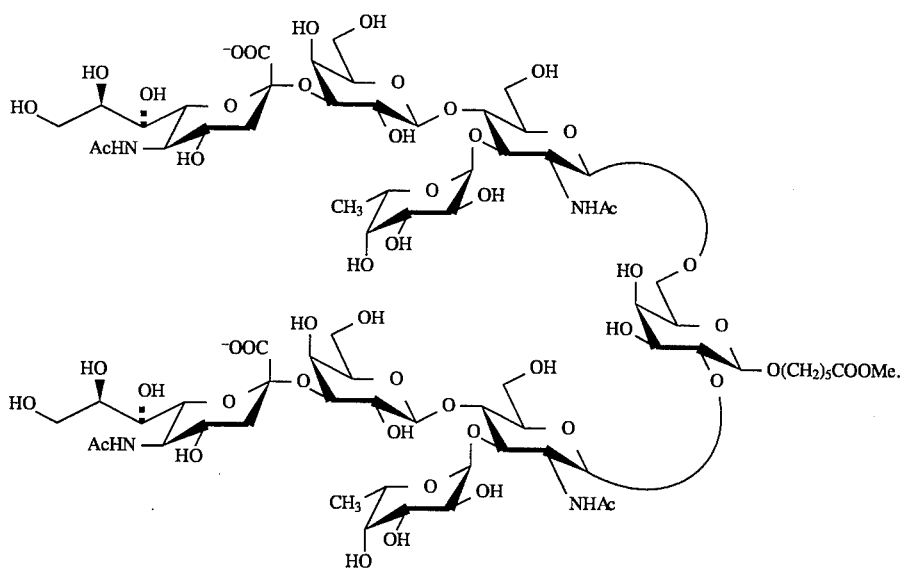

18. The compound according to claim 15 that corresponds to the formula

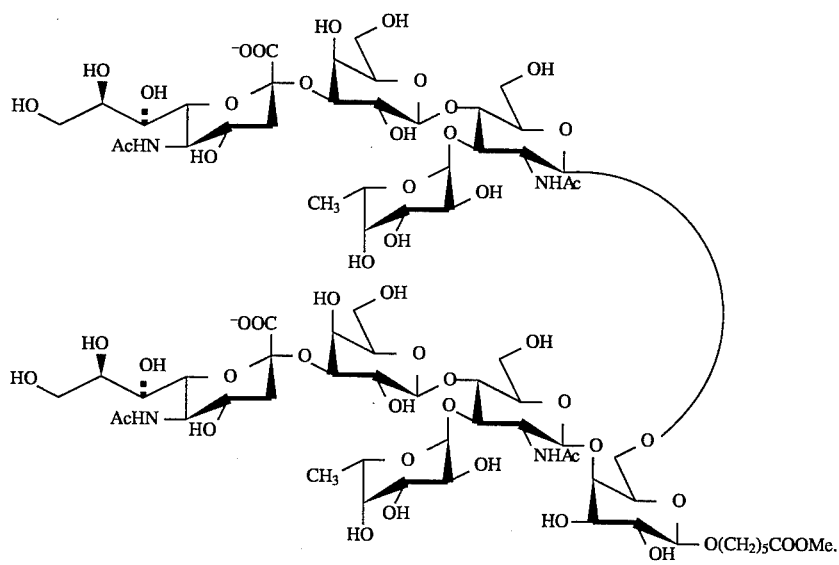

19. A pharmaceutical composition comprising an amount of a bivalent sialyl Lewis X saccharide sufficient to inhibit the binding of cells that express sialyl Le X on their surfaces to selectin, said bivalent sialyl Lewis X saccharide being dissolved or dispersed in a pharmaceutically acceptable diluent and having the structure

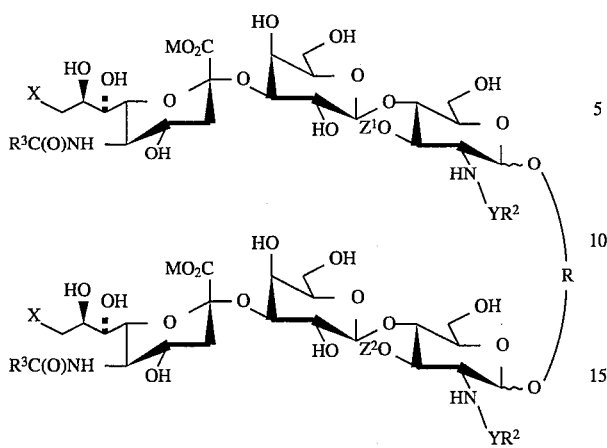

wherein R is a directly linked bivalent monosaccharide unit;

Y is selected from the group consisting of C(O), SO$_2$, HNC(O), OC(O) and SC(O);

R$^2$ is selected from the group consisting of a C$_1$–C$_6$ aliphatic, an aryl, a substituted aryl and a phenyl C$_1$–C$_3$ alkylene group, wherein said aryl group has one six-membered aromatic ring or two fused six-membered aromatic rings, which ring or rings are hydrocarbyl, monoazahydrocarbyl, or diazahydrocarbyl rings, and said substituted aryl group is a before-mentioned aryl group having a substituent selected from the group consisting of halo, trifluoromethyl, nitro, C$_1$–C$_6$ alkyl, C$_1$–C$_6$ alkoxy, amino, mono-C$_1$–C$_6$ alkylamino, di-C$_1$–C$_6$ alkylamino, benzylamino and C$_1$–C$_6$ alkylbenzylamino;

R$^3$ is methyl or hydroxymethyl;

X is selected from the group consisting of hydroxyl, C$_1$–C$_6$ acyloxy, C$_2$–C$_6$ hydroxylacyloxy, halo and azido;

Z$^1$ and Z$^2$ are α-L-fucosyl or hydrogen (H), out at least one of Z$^1$ and Z$^2$ is α-L-fucosyl; and M is a proton (H$^+$) or a pharmaceutically acceptable cation.

20. The pharmaceutical composition according claim 19 wherein Z$^2$ is hydrogen.

21. The pharmaceutical composition according to claim 19 wherein Z$^1$ is hydrogen.

22. The pharmaceutical composition according to claim 19 wherein both Z$^1$ and Z$^2$ are α-L-fucosyl.

23. The pharmaceutical composition according to claim 19 wherein R has a structure selected from the group consisting of

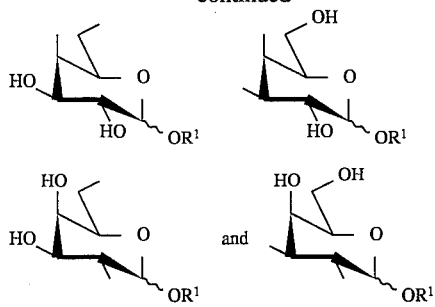

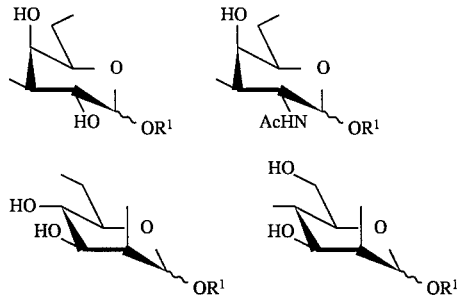

wherein R$^1$ is selected from the group consisting of hydrogen, a C$_1$–C$_{18}$ straight chain, branched chain or cyclic hydrocarbyl, a C$_1$–C$_6$ alkyl C$_1$–C$_5$ alkylene ω-carboxylate, and an ω-tri(C$_1$–C$_4$ alkyl/phenyl)silyl C$_2$–C$_4$ alkylene group, or OR$^1$ together form a C$_1$–C$_{18}$ straight chain, branched chain or cyclic hydrocarbyl carbamate.

24. A process for inhibiting adhesion between selectin and cells that express sialyl Le X on their surfaces that comprises admixing selectin, and cells that express sialyl Le X on their surfaces in an aqueous medium with an adhesion-inhibiting amount of a bivalent SLe$^x$ saccharide compound having the formula

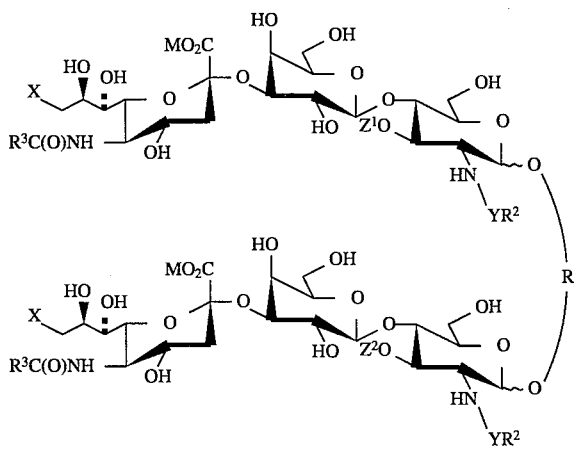

wherein R is a directly linked divalent monosaccharide unit;

Y is selected from the group consisting of C(O), SO$_2$, HNC(O), OC(O) and SC(O);

R$^2$ is selected from the group consisting of a C$_1$–C$_{18}$ aliphatic, an aryl, a substituted aryl and a phenyl C$_1$–C$_3$ alkylene group, wherein said aryl group has one six-membered aromatic ring or two fused six-membered aromatic rings, which ring or rings are hydrocarbyl, monoazahydrocarbyl, or diazahydrocarbyl rings, and said substituted aryl group is a before-mentioned aryl group having a substituent selected from the group consisting of halo, trifluoromethyl, nitro, C$_1$–C$_6$ alkyl, C$_1$–C$_6$ alkoxy, amino, mono-C$_1$–C$_6$ alkylamino, di-C$_1$–C$_6$ alkylamino, benzylamino and C$_1$–C$_6$ alkylbenzylamino;

R$^3$ is methyl or hydroxymethyl;

X is selected from the group consisting of hydroxyl, C$_1$–C$_6$ acyloxy, C$_2$–C$_6$ hydroxylacyloxy, halo and azido;

Z$^1$ and Z$^2$ are α-L-fucosyl or hydrogen (H), but at least one of Z$^1$ and Z$^2$ is α-L-fucosyl; and M is a proton (H$^+$) or a pharmaceutically acceptable cation.

25. The process according to claim 24 wherein R has a structure selected from the group consisting of

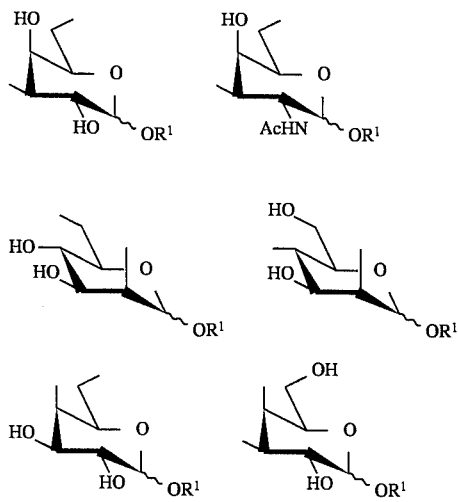
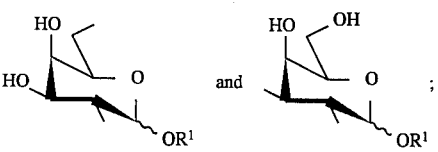

wherein $R^1$ is selected from the group consisting of hydrogen, a $C_1$–$C_{18}$ straight, branched chain or cyclic hydrocarbyl, a $C_1$–$C_6$ alkyl $C_1$–$C_5$ alkylene ω-carboxylate, and a ω-tri($C_1$–$C_4$ alkyl/phenyl)silyl $C_2$–$C_4$ alkylene group, or $OR^1$ together form a $C_1$–$C_{18}$ straight chain, branched chain or cyclic hydrocarbyl carbamate.

26. The process according to claim 24 wherein both $Z^1$ and $Z^2$ are α-L-fucosyl.

27. The process according to claim 24 wherein said selectin is recombinant E-selectin containing the amino-terminal 527 amino acid residues of native E-selectin and lacking the transmembrane domain of that molecule, said recombinant selectin being bound to a solid support.

* * * * *